United States Patent [19]

Moscow et al.

[11] Patent Number: 5,716,788
[45] Date of Patent: Feb. 10, 1998

[54] ANTIBODIES TO HUMAN REDUCED FOLATE CARRIER PROTEIN

[75] Inventors: Jeffrey A. Moscow, Silver Spring; Kenneth H. Cowan, Potoma; Kathy Dixon, Olney; Rui He, Germantown, all of Md.

[73] Assignee: The United States of America as represented by the Department of Health and Human Services, Washington, D.C.

[21] Appl. No.: 484,840

[22] Filed: Jun. 7, 1995

[51] Int. Cl.$^6$ ............... C07K 16/00; G01N 33/53; G01N 33/567; G01N 33/573

[52] U.S. Cl. ............... 435/7.1; 435/7.21; 435/7.4; 435/7.7; 530/388.1; 530/388.22; 530/391.3; 530/387.1

[58] Field of Search ............... 530/387.1, 388.1, 530/391.3; 435/7.1, 7.9, 7.21, 7.4, 7.7

[56] References Cited

U.S. PATENT DOCUMENTS 4,358,535  11/1982  Falkow et al. ............... 435/5
4,946,778  8/1990  Ladner et al. ............... 435/69.6

FOREIGN PATENT DOCUMENTS

WO 91/11465  8/1991  WIPO.

OTHER PUBLICATIONS

Prasad et al. Biochem Biophys Res Comm 206:681–87, Jan. 17, 1995.

Williams & Flintoff, J. Biol Chem. 270:2987–92, Feb. 17, 1995.

Sambrook et al. *Molecular Cloning, A Laboratory Manual*, 2nd edit. Cold Spr. Harbor Lab Press, 1989.

Harlow & Lane, *Antibodies, A Laboratory Manual*, Cold Spr. Harbor Lab Press, 1988.

Prasad et al., "Molecular Cloning of the Human Placental Folate Transporter", Biochem. & Biophys. Research Comm., vol. 206, No. 2, (1995) pp. 681–687.

Williams et al., "Isolation of a Human cDNA That Complements a Mutant Hamster Cell Defective in Methotrexate Uptake", Journal of Biological Chem., vol. 270, No. 7, (1995), pp. 2987–2992.

Wong et al., "Cloning and Characterization of a Human Reduced Folate Carrier (RFC) cDNA From Transport Up-Regulated K562 Cells", Proc. of the American Asso. for Cancer Res., vol. 36, (1995) pp. 381 & 379.

Wong et al., "Isola. Human cDNAs Restore Methotrexate Sens. & Reduced Folate Carrier Activ. in Methot. Trans.–defective Chinese Hamster Ovary Cells", J. Biol. Chem., vol. 270, No. 29, (1995), pp. 17468–17475.

Moscow et al., "Isola. of a Gene Encoding a Human Reduced Folate Carrier (RFC1) & Analysis of Its Expression in Trans.–deficient, Methot.–resis. Human Breast Cancer Cells", Canc. Res., vol. 55, (1995), pp. 3790–3794.

Matherley et al., "Charact. of Trans.–mediated Methot. Resis. Human Tumor Cells w/Antibodies to Membrane Carr. for Methot. & Tetrahydrofolate Cofact.", J. Biol. Chem., vol. 267, No. 32, (1992), pp. 23253–23260.

Henderson, et al. *Mediated Uptake of Folate by a High–Affinity Binding Protein in Sublines of L1210 Cells Adapted to Nonomolar Concentrations of Folate*, J. Membrane Biol. 101:247–258 (1988).

Dixon, et al. *A Novel cDNA Restores Reduced Folate Carrier Activity and Methotrexate Sensitivity to Transport Deficient Cells*, J. Bio. Chem. 269:17–20 (1994).

Coligan, et al. *Current Protocols in Molecular Biology*, Copyright 1991 by Current Protocols.

Wosnick, et al. *Rapid construction of large synthetic genes: total chemical synthesis of two different versions of the bovine prochymosin gene*, Gene 60:115–127 (1987).

Adang, et al. *The reconstruction and expression of a Bacillus thuringiensis cryIIIA gene in protoplasts and potato plants*. Plant Mole. Biol. 21:1131–1145 (1993).

Hamer, et al. *Regulation In Vivo of a Cloned Mammalian Gene: Cadmium Induces the Transcription of a Mouse Metallothionein Gene in SV40 Vectors*, J. Molec. Appl. Genet. 1: 273–288 (1982).

McKnight *Functional Relationships between Transcriptional Control Signals of the Thymidine Kinase Gene of Herpes Simplex Virus*, Cell 31: 355–365 (1982).

Benoist, et al. *In Vivo sequence requirements of the SV40 early promoter region*, Nature 290: 304–310 (1981).

Gorman, et al. *The Rous sarcoma virus long terminal repeat is a strong promoter when introduced into a variety of eukaryotic cells by DNA–mediated tansfection*, Proc. Nat'l. Acad. Sci. USA 79:6777–6781 (1982).

Foecking, et al. *Powerful and versatile enhancer–promoter unit for mammalian expression vectors*, Gene 45:101–105 (1980).

Zhou, et al. *Synthesis of Functional mRNA in Mammalian Cells by Bacteriophage T3 RNA Polymerase*, Mol. Cell. Biol. 10:4529–4537 (1990).

Kaufman, et al. *Improved vectors for stable expression of foreign genes in mammalian cells by use of the untranslated leader sequence from EMC virus*, Nucl. Acids Research 19:4485–4490 (1991).

(List continued on next page.)

*Primary Examiner*—Lila Feisee
*Assistant Examiner*—Ray F. Ebert
*Attorney, Agent, or Firm*—Spencer & Frank

[57] ABSTRACT

One shortcoming of methotrexate chemotherapy is that previously responsive tumors can become refractory to methotrexate after continued exposure. Such methotrexate resistance may be due to underexpression of reduced folate carrier (RFC) protein. The present invention provides DNA molecules encoding human RFC. The present invention also relates to expression vectors comprising RFC-encoding DNA molecules, and to the use of such vectors to restore methotrexate sensitivity in mammalian cells. The present invention further relates to antibodies that bind with human RFC protein, and to methods of detecting human RFC protein using such antibodies.

7 Claims, 5 Drawing Sheets

OTHER PUBLICATIONS

Wetmur, et al. *Kinetics of Renaturation of DNA*, J. Mol. Biol. 31:349–370 (1968).

Sharp, et al. *Viral DNA in Transformed Cells*, J. Mol. Biol. 86:709–726 (1974).

Britten, et al. *Repeated Sequences in DNA*, Science 161:529–540 (1968).

Sutton *A Crude Nuclease Preparation Suitable for Use in DNA Reassociation Experiments*, Biochim. Biophys. Acta 240:522–530 (1971).

Rosenberg, et al. *Grafting Genetically Modified Cells to the Damaged Brain: Restorative Effects of NGF Expression*, Science 242:1575–1578 (1988).

Wolff, et al. *Grafting fibroblasts genetically modified to produce L–dopa in a rat model of Parkinson disease*, Proc. Natl. Acad. Sci 86:9011–9014 (1989).

Hodgson *The Vector Void in Gene Therapy*, Bio/Technology 13:222 (1995).

Caplen, et al. *Liposome–mediated CFTR gene transfer to the nasal epithelium of patients with cystic fibrosis*, Nature Medicine 1:39–46 (1995).

Berkner *Development of Adenovirus Vectors for the Expression of Heterlogous Genes*, BioTechniques 6:616–629 (1988).

Quantin, et al. *Adenovirus as an expression vector in muscle cells in vivo*, Proc. Natl. Acad. Sci. 89:2581–2584 (1992).

Lebkowski, et al. *Adeno–Associated Virus: a Vector System for Efficient Introduction and Integration of DNA into a Variety of Mammalian Cell Types*, Molecular and Cellular Biology 8:3988–3996 (1996).

Breakefield, et al. *Gene Transfer into the Nervous System*, Molecular Neurobiology 1:339–371 (1987).

Shih, et al. *Herpes Simplex Virus as a Vector for Eukaryotic Viral Genes*, Vaccines 85:177–180 (Cold Spring Harbor Press 1985).

Wolff, et al. *Expression of retrovirally transduced genes in primary cultures of adult rat hepatocytes*, Proc. Nat'l. Acad. Sci. 84:3344–3348 (1989).

Bender, et al. *Evidence that the Packaging Signal of Moloney Murine Leukemia Virus Extends into the gag Region*, Journal of Virology, 61:1639–1646 (1987).

Armentano, et al. *Effect of Internal Viral Sequences on the Utility of Retroviral Vectors*, Journal of Virology, 61:1647–1650 (1987).

Markert, et al. *Expanded spectrum of viral therapy in the treatment of nervous system tumors*, J. Neurosurg. 77:590–594 (1992).

Culver *Clinical Applications of Gene Therapy for Cancer*, Clin. Chem. 40:510–512 (1994).

Oldfield, et al. *Gene Therapy for the Treatment of Brain Tumors Using Intra–Tumoral Transduction with the Thymidine Kinase Gene and Intravenous Ganciclovir*, Hum. Gene Ther. 4:39–69 (1993).

Bi, et al. *In Vitro Evidence that Metabolic Cooperation Is Responsible for the Bystander Effect Observed with HSV tk Retroviral Gene Therapy*, Human Gene Therapy 4:725–731 (1993).

Martuza, et al. *Experimental Therapy of Human Glioma by Means of a Genetically Engineered Virus Mutant*, Science 252:854–856 (1991).

Green, et al. *Production of Polyclonal Antisera*, Immunochemical Protocols (Manson, ed.), pp. 1–5 (Humana Press 1992).

Kohler and Milstein *Continuous cultures of fused cells secreting antibody of predefined specificity*, Nature 256:495–497 (1975).

Baines, et al. *Purification of Immunoglobulin G (IgG)*, Methods in Molecular Biology, vol. 10, pp. 79–104 (Human Press, Inc. 1992).

Coligan, et al. (eds.), *Production of Monoclonal Antibodies*, Current Protocols in Immunology, vol. 1, pp. 2.5.1–2.6.7 (John Wiley & Sons 1991).

Losman, et al. *Baboon Anti–Idiotype Antibodies Mimic a Carcinoembryonic Antigen Epitope*, Int. J. Cancer 46:310–314 (1990).

Orlandi, et al. Proc. Nat'l. Acad. Sci. USA 86:3833 (1989).

Jones, et al. *Replacing the complementarity–determining regions in a human antibody with those from a mouse*, Nature 321:522 (1986).

Riechmann, et al. *Reshaping human antibodies for therapy*, Nature 332:323–327 (1988).

Verhoeyen, et al. *Reshaping Human Antibodies: Grafting an Antilysozyme Activity*, Science 239:1534–1536 (1988).

Carter, et al. *Humanization on an anti–p185$^{HER2}$ antibody for human cancer therapy*, Proc. Nat'l. Acad. Sci. USA 89:4285–4289 (1992).

Sandhu *Protein Engineering of Antibodies*, Critical Reviews in Biotechnology 12:437–462 (1992).

Singer, et al. *Optimal Humanization of 1B4, an Anti–CD18 Murine Monoclonal Antibody, Is Achieved by Correct Choice of Human V–Region Framework Sequences*, Journal of Immunology 150:2844–2857 (1993).

Barbas,et al. *Combinatorial Immunoglobulin Libraries on the Surface of Phage (Phabs): Rapid Selection of Antigen–Specific Fabs*, Methods: A Companion to Methods in Enzymology 2:119–123 (1991).

Winter, et al. *Making Antibodies by Phage Display Technology*, Annu. Rev. Immunol. 12:433–455 (1994).

Green, et al. *Antigen–specific human monoclonal antibodies from mice engineered with human Ig heavy and light chain YACs*, Nature Genetics 7:13–21 (1994).

Lonberg, et al. *Antigen–specific human antibodies from mice comprising four distinct genetic modifications*, Nature 368:856–859 (1994).

Taylor, et al. *Human immunoglobin transgenes undergo rearrangement, somatic mutation and class switching in mice that lack endogenous IgM*, International Immunology 6:579–591 (1994).

Nisonoff, et al. *Separation of Univalent Fragments from the Bivalent Rabbit Antibody Molecule by Reduction of Disulfide Bonds* Archives of Biochemistry and Biophysics 89:230–244 (1960).

Porter *The Hydrolysis of Rabbit γ–Globulin and Antibodies with Crystalline Papain*, Biochem. J. 73:119–127 (1959).

Inbar et al. *Localization of Antibody–Combining Sites within the Variable Portions of Heavy and Light Chains*, Proc. Nat. Acad. Sci. USA 69:2659–2662 (1972).

Whitlow, et al. *Single–Chain Fv Proteins and Their Fusion Proteins*, Methods: A Companion to Methods in Enzymology 2:97–105 (1991).

Bird, et al. *Single–Chain Antigen–Binding Proteins*, Science 242:423–426 (1988).

Pack, et al. *Improved Bivalent Miniantibodies, with Identical Avidity as Whole Antibodies, Produced by High Cell Density Fermentation of Eschericia coli*, Bio/Technology 11:1271–1277 (1993).

Larrick, et al. *PCR Amplification of Antibody Genes*, Methods: A Companion to Methods in Enzymology 2:106–110 (1991).

Ponder *Cell Marking Techniques and Their Application*, Mammalian Development: A Practical Approach, Monk (ed.) pp. 115–38 (IRL Press 1987).

Volm, et al. *Detection of the Multidrug Resistant Phenotype in Human Tumours by Monoclonal Antibodies and the Streptavidin–Biotinylated Phycoerythrin*.

Dixon, et al. *Folate Transport and the Modulation of Antifolate Sensitivity in a Methotrexate–Resistant Human Breast Cancer Cell Line*, Cancer Commun. 3:357–365 (1991).

Williams, et al. *Isolation of a Hamster cDNA Clone Coding for a Function Involved in a Methotrexate Uptake*, J. Biol. Chem. 269:5810–5816 (1994).

Dutrillaux and Lejeune *New Techniques in the Study of Human Chromasomes: Methods and Applications*, Adv. Hum. Genet. 5:119–155 (1975).

Pinkel, et al. *Fluorescence in situ hybridization with human chromosome–specific libraries: Detection of trisomy 21 and translocations of chromosome 4*, Proc. Nat'l. Acad. Sci. USA 85:9138–9142 (1988).

Laemmli Nature 227:680–(1970).

Zhu, et al. *Sytemic Gene Expression After Intravenous DNA Delivery into Adult Mice*, Science 261:209–211.

Bambot, et al. PCR Methods and Applications 2: 266 (1993).

Stein, et al. *Specificity and Properties of MAb RS7–3G11 and the Antigen Defined by this Pancarcinoma Monoclonal Antibody*, Int. J. Cancer 55:938–946.

Bayer, et al. *Immunochemical Applications of Avidin–Biotin Technology*, in Methods in Molecular Biology, vol. 10, Manson (ed.), pp. 149–162 (Human Press,, 1992).

```
                                    20                    40                    60
HUMAN    MVPSSPAVEK QVPVEPGPDP ELRSWRRLVC YLCFYGFMAQ IRPGESFITP YLLGPDKNFT
MURINE   ^^^tgqva^^ ^aye^^rq^h ^^k^^^c^^f ^^^^f^^^^^ ^^^^^^^^^^ f^^--erk^^
HAMSTER  ^^^tgqva^^ ^ace^^rq^r ^^k^^^c^^f ^^^^f^^^^^ ^^^^^^^^^^ ^^^--qq^^^
                                    80                   100                   120
HUMAN    RDEVTNEITP VLSYSYLAVL VPVFLLTDYL RYTPVLLLQG LSFVSVWLLL LLGHSVAHMQ
MURINE   keq^^^^^i^ m^p^^h^^^^ ^^^^^^^^^^ ^^k^^^v^^c ^^^^c^^^^^ ^^^t^^v^^^
HAMSTER  ieq^^^^^i^ ^^p^^h^^^^ ^^i^^^^^^^ ^^k^i^i^^c ^^^mc^^^^^ ^^^t^^v^^^
                                   140                   160                   180
HUMAN    LMELFYSVTM AARIAYSSYI FSLVRPARYQ RVAGYSRAAV LLGVFTSSVL GQLLVTVGRV
MURINE   ^^^v^^^^^^ ^^^^^^^^^^ ^^^^h^s^^^ ^m^s^^^^^^ ^^^^^i^^^^ ^^q^^^^^hi
HAMSTER  ^^^v^^^^^^ ^^^^^^^^^^ ^^^^^^s^^^ ^m^s^^^^^^ ^^^^^^^^^^ ^^v^leqksq
                                   200                   220                   240
HUMAN    SFSTLNYISL AFLTFSVVLA LFLKRPKRSL FFNRDDRGRC ETSASELERM NPGPGGKLGH
MURINE   ^ty^^^cv^^ g^il^^l^^s ^^^^^^^^^^ ^^^^stla^- galpc^^dq^ n^^^dr^^dr
HAMSTER  nsnm^^^^^^ g^ii^^lg^s ^^^^^^h^^ ^^^^salvh- kalpc^^dq^ h^^^^^^er
                                   260                   280                         rpep 300
HUMAN    ALRVACGDSV LARMLRELGD SLRRPQLRLW SLWWVFNSAG YYLVVYYVHI LWNEVDPTTN
MURINE   m^-gt^r^^f ^v^^^s^^ve na^q^^^^^^ c^^^^^^^s^ ^^^it^^^^v ^^rst^ssl-
HAMSTER  v^-gs^rn^f ^vc^^s^^vg n^^q^hv^^^ c^^^^^^^^^ ^^^i^^^^^v ^^s-i^---k
                                   320                   340                   360
HUMAN    SARVYNGAAD AASTLLGAIT SFAAGFVKIR WARWSKLLIA GVTATQAGLV FLLAHTRHPS
MURINE   ^----^^^^v^ ^^^^^^s^^^ ^^s^^^ls^^ ^tl^^^^v^^ ^^i^i^^s^^ ^cmfqi^d--
HAMSTER  nln-^^^^v^ ^^^^^^s^^^ ^^s^^^^^^^ ^^^^^^v^^ s^i^i^^^^^ ^mvhyvtwvh
                                   380                   400                   cmy     420
HUMAN    SIWLCYAAFV LFRGSYQFLV PIATFQIASS LSKELCALVF GVNTFFATIV KTIITFIVSD
MURINE   -^^^v^^vt^^ ^^^^a^^^^^ ^^^^^^^^^^ ^^^^^^^^^^ ^i^^^^^^fl l^df^lv^^^
HAMSTER  k^^vl^mty^ ^^^^a^^^^^ ^^^^^^^^^^ ^^^^^^^^^^ ^i^^^^^^al ^^a^^lv^^^
                                   440                   460                   480
HUMAN    VRGLGLPVRK QFQLYSVYFL ILSIIYFLGA MLDGLRDCQR GHHPRQPPAQ GLRSAAEEKA
MURINE   k^^^^^q^^d ^^ri^fi^^^ m^^^tc^dw^ g^^^^^y^^^ ^r^qplaq^^ e^^^pl-^ts
HAMSTER  k^^^^^k^e^ ^^ci^^^^^m v^^v^c^v^^ v^^^v^y^r^ ^r^qpl^lp^ e^-^pl-^ns
                                   500                   520                   540
HUMAN    AQRLSVQDKG LGGLQPAQSP PLSPEDSLGA VGPASLEQRQ SDPYLAQAPA PQAAEFLSPV
MURINE   v^ai^l^^gd ^r^p^^s-a^ q^ls^^gmed -drgd^^*
HAMSTER  v^vp^m^^r^ ^^^^^^s-a^ q^l^^^gved -se^^^*
                                   560                   580
HUMAN    TTPSPCTLSS AQASGPEAAD ETCPQLAVHP PGVSKLGLQC LPSDGVQNVN Q*
```

ANTIBODIES TO HUMAN REDUCED FOLATE CARRIER PROTEIN

BACKGROUND OF THE INVENTION

The present invention relates to a gene encoding reduced folate carrier (RFC). The invention further relates to methods for the treatment of methotrexate-resistant, transport-deficient cancer cells by introducing into such cells the gene encoding RFC.

Methotrexate (MTX) is a folate antagonist effective in the treatment of various cancers such as non-Hodgkin's lymphoma, childhood acute lymphoblastic leukemia, osteosarcoma and breast cancer. One shortcoming of MTX drug therapy is that previously responsive tumors can become refractory to MTX after continued exposure. This clinically observable effect is readily reproducible in vitro by selecting cells in increasing concentrations of MTX. Although resistance to MTX in in vitro models can result from over-expression of the target enzyme dihydrofolate reductase, alteration of dihydrofolate reductase affinity for MTX, decreased folylpolyglutamate synthase, and decreased thymidylate synthase levels, decreased MTX uptake is the principal characteristic in many MTX-resistant cell lines.

In contrast to bacteria, animal cells are incapable of synthesizing folate compounds, which are nutritionally required for survival and growth. Animal cells therefore possess mechanisms for the uptake of folate from their environment. Two pathways for folate transport across cell membranes have been described. The first occurs via the folate receptor, and the second occurs via RFC. These uptake mechanisms are distinguishable functionally based on their relative affinities for folic acid and reduced folates respectively. The folate receptor has a higher affinity for folic acid than for reduced folates, whereas RFC has a greater affinity for reduced folates than for folic acid. Both systems, however, are capable of facilitating MTX uptake.

RFC has a relatively lower affinity for MTX (0.3 to 4 μM) than the folate receptor (74 to 200 nM). Cells that do not express RFC require higher concentrations of reduced folate compounds for growth than cells that do. See Henderson et al., *J. Membr. Biol.* 101: 347 (1988). In addition, RFC protects cells from the cytotoxic effects of lipophilic folate antagonists, such as trimetrexate, when grown in the presence of reduced folate compounds. See Dixon et al., *J. Biol. Chem.* 287: 24140 (1992).

MTX resistance coincides with decreased RFC activity in transport-mediated MTX resistance. Decreased RFC activity has been observed in MTX-resistant, transport-deficient cell lines, including murine L1210 leukemia cell lines, human leukemia cell lines, Chinese hamster ovary cells and human MTX$^R$ ZR-75-1 breast cancer cells. The transfection of a murine RFC gene partially reversed MTX resistance in the MTX$^R$ ZR-75-1 cells, and transfection of the hamster homologue reversed MTX resistance in a Chinese hamster ovary cell line.

The foregoing discussion reveals the need to alleviate the problem of developing resistance to methotrexate by various cancer cells in order to facilitate the continued effectiveness of the drug in the treatment of these cancers. As indicated, this effectiveness depends upon the sensitivity of the target cancer cells to MTX, which in turn depends upon the RFC activity in those cells. Absent the ability to prevent outright the development of MTX resistance in cancer cells, the re-establishment of MTX sensitivity by restoring RFC activity is highly advantageous. Methods of treating MTX-resistant, transport-deficient cancer cells through gene therapy are even more desirable. Prior to the disclosure of the invention here, no means for accomplishing such tasks have been reported.

SUMMARY OF THE INVENTION

Accordingly, an objective of the present invention is the isolation of a gene encoding RFC. A further objective of the invention is to provide methods for the treatment of MTX-resistant, transport-deficient cancer cells by introducing into such cells the gene encoding RFC. The purpose of this gene therapy is to restore RFC activity, and thereby re-establish the sensitivity of these cancer cells to MTX drug treatment.

These and other objects are achieved, in accordance with one embodiment of the present invention by the provision of an isolated DNA molecule encoding human reduced folate carrier protein (RFC), wherein the DNA molecule comprises a nucleotide sequence that encodes either:

(a) a polypeptide having the amino acid sequence of SEQ ID NO: 2, or (b) a polypeptide that is an RFC variant protein, wherein the product of the DNA molecule has the function of a reduced folate carrier protein. A suitable DNA molecule comprises a nucleotide sequence that encodes a polypeptide having the amino acid sequence of SEQ ID NO: 2. Such a DNA molecule comprises the nucleotide sequence of SEQ ID NO: 1.

The present invention also is directed to expression vectors comprising a promoter that is operably linked with such DNA molecules, wherein the expression vectors produce human reduced folate carrier protein.

The present invention is further directed to a method of using such an expression vector to prepare reduced folate carrier protein, comprising the steps of:

(a) introducing the expression vector into a host cell to produce a recombinant host cell, (b) culturing the recombinant host cell, and (c) isolating the reduced folate carrier protein from the cultured recombinant host cell.

The present invention also is directed to methods for enhancing the uptake of methotrexate by a mammalian cell, comprising the step of introducing an RFC expression vector into the cell.

The present invention is further directed to a method of inhibiting the growth of a tumor in a mammal, comprising the steps of:

(a) administering an RFC expression vector to the mammal, wherein cells of the mammal containing the expression vector produce reduced folate carrier protein that is encoded by the expression vector, and (b) administering methotrexate to the mammal.

The present invention also contemplates such methods wherein the expression vector is contained within a virion.

The present invention also is directed to a method of detecting the presence of RFC RNA in a mammalian tissue sample, comprising the steps of:

(a) contacting the tissue sample with a DNA molecule encoding RFC protein under conditions of hybridization, and (b) detecting the formation of a hybrid of the DNA molecule and the RFC RNA.

The present invention further is directed to antibodies that bind with human reduced folate carrier (RFC) protein, wherein the RFC protein comprises a polypeptide having the amino acid sequence of SEQ ID NO: 2. Such antibodies may be polyclonal or monoclonal.

3

The present invention also is directed to a method of using such antibodies to detect the presence of RFC protein in a biological sample, comprising the steps of:

(a) contacting the biological sample with at least one of such antibody, and (b) detecting any of the antibody bound to the biological sample.

Suitable detection methods include the technique of in situ hybridization.

The present invention is further directed to a reduced folate carrier (RFC) immunoconjugate comprising:

(a) an antibody or an antibody fragment that binds with RFC protein, and (b) a diagnostic agent.

A suitable diagnostic agent is selected from the group consisting of radioactive label, photoactive agent or dye, fluorescent label, enzyme label, bioluminescent label, chemiluminescent label and colloidal gold.

BRIEF DESCRIPTION OF THE DRAWINGS

FIG. 2A–B shows the results of analyses of the RFC gene. Part A presents the nucleotide sequence of the coding region of RFC1, including 18 nucleotides of the 5' untranslated region (UTR) and 200 nucleotides of the 3' UTR [SEQ ID NO: 1], as well as the predicted amino acid sequence [SEQ ID NO: 2]. Part B shows a Kyte-Doolittle hydrophilicity plot of the predicted human RFC1 protein.

FIG. 3 shows a comparison between the amino acid sequence of the predicted RFC1 protein (SEQ ID NO: 2) and the amino acid sequences of the murine (SEQ ID NO: 3) and hamster (SEQ ID NO: 4) homologues The symbol (^) represents the identical amino acid residue at that position in the mouse and/or hamster sequence when compared to the human sequence. The symbol (–) represents the absence of a corresponding amino acid residue at that position in the mouse and/or hamster sequence when compared to the human sequence. The symbol (*) represents the terminus of the polypeptide.

DETAILED DESCRIPTION OF THE PREFERRED EMBODIMENTS

1. Isolation of DNA Molecules Encoding Reduced Folate Carrier Protein

Figure 2A:
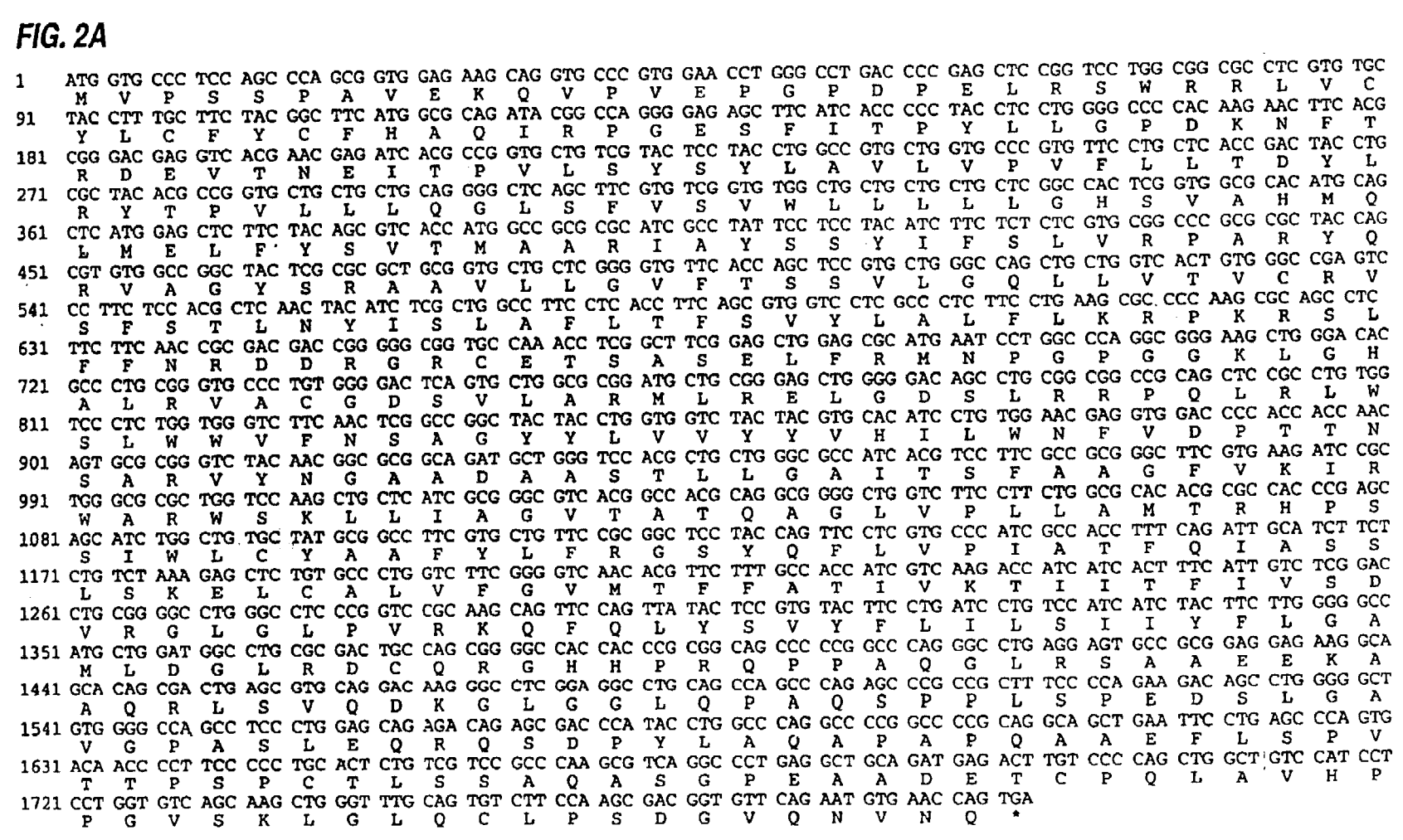
Figure 2B:
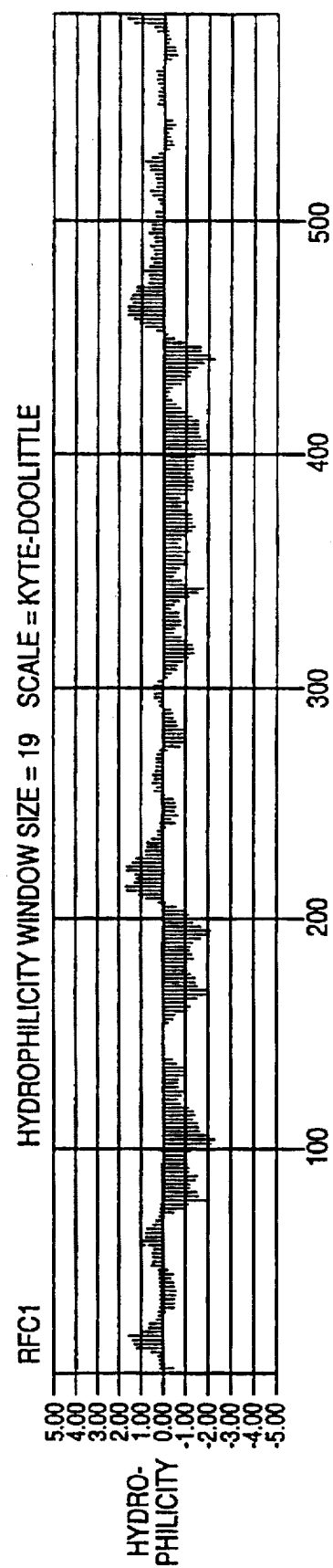

A murine RFC cDNA clone was isolated by a functional screening technique in which reduced folate carrier activity and methotrexate sensitivity were restored to a methotrexate-resistant, transport-deficient human breast cancer cell line. Dixon et al. *J. Biol. Chem.* 269: 17 (1994). As described herein, the murine RFC clone was used as a probe to isolate DNA molecules encoding the human RFC gene. See Example 1. The nucleotide sequence of the human RFC gens [SEQ ID NO: 1], and the predicted, corresponding amino acid sequence [SEQ ID NO: 2] are shown in FIG. 2.

4

Accordingly, the present invention contemplates DNA molecules having the nucleotide sequence of SEQ ID NO: 1, as well as polypsprides having the amino acid sequence of SEQ ID NO: 2.

The present invention also includes DNA molecules that encode a polypeptide having an amino acid sequence of SEQ ID NO: 2. Using this amino acid sequence, those of skill in the art can readily determine the nucleotide sequences of suitable DNA molecules.

The present invention also contemplates variants of the polypeptide having the amino acid sequence of SEQ ID NO: 2. The amino acid sequences of such RFC variants contain conservative amino acid substitutions of the amino acid sequence of SEQ ID NO: 2. Those of skill in the art are aware of such conservative substitutions. Such RFC variants must function as reduced folate carrier proteins. This function can be ascertained, for example, by transfecting methotrexate-resistant cells that underexpress RFC with DNA molecules encoding RFC variants, as described in Example 6.

The present invention also includes expression vectors comprising human RFC-encoding sequences. Such expression vectors can be used, for example, to produce RFC protein for production of antibodies, as described below. DNA molecules encoding human RFC can be obtained by screening cDNA or genomic libraries with polynucleotide probes having nucleotide sequences based upon SEQ ID NO: 1.

Alternatively, RFC genes can be obtained by synthesizing DNA molecules using mutually priming long oligonucleotides. See, for example, Ausubel et al., (eds.), CURRENT PROTOCOLS IN MOLECULAR BIOLOGY, pages 8.2.8 to 8.2.13 (1990) ["Ausubel"]. Also, see Wosnick et al., *Gene* 60: 115 (1987). Current techniques using the polymerase chain reaction provide the ability to synthesize genes as large as 1.8 kilobases in length. Adang et al., *Plant Molec. Biol.* 21: 1131 (1993); Bambot et al., *PCR Methods and Applications* 2: 266 (1993).

Expression vectors that are suitable for production of RFC protein typically contain (1) prokaryotic DNA elements coding for a bacterial replication origin and an antibiotic resistance marker to provide for the growth and selection of the expression vector in a bacterial host; (2) eukaryotic DNA elements that control initiation of transcription, such as a promoter; and (3) DNA elements that control the processing of transcripts, such as a transcription termination/polyadenylation sequence. RFC protein of the present invention preferably is expressed in eukaryotic cells, such as mammalian, insect and yeast cells. Mammalian cells are especially preferred eukaryotic hosts because mammalian cells provide suitable post-translational modifications such as glycosylation. Examples of mammalian host cells include Chinese hamster ovary cells (CHO-K1; ATCC CCL61), rat pituitary cells ($GH_1$; ATCC CCL82), HeLa S3 cells (ATCC CCL2.2), rat hepatoma cells (H-4-II-E; ATCC CRL1548) SV40-transformed monkey kidney cells (COS-1; ATCC CRL 1650) and murine embryonic cells (NIH-3T3; ATCC CRL 1658).

For a mammalian host, the transcriptional and translational regulatory signals may be derived from viral sources, such as adenovirus, bovine papilloma virus, simian virus, or the like, in which the regulatory signals are associated with a particular gene which has a high level of expression. Suitable transcriptional and translational regulatory sequences also can be obtained from mammalian genes, such as actin, collagen, myosin, and metallothionein genes.

Transcriptional regulatory sequences include a promoter region sufficient to direct the initiation of RNA synthesis. Suitable eukaryotic promoters include the promoter of the mouse metallothionein I gene (Hamer et al., *J. Molec. Appl. Genet.* 1: 273 (1982)]; the TK promoter of Herpes virus [McKnight, *Cell* 31: 355 (1982)]; the SV40 early promoter [Benoist et al., *Nature* 290: 304 (1981)]; the Rous sarcoma virus promoter [Gorman et al., *Proc. Nat'l Acad. Sci. USA* 79: 6777 (1982); and the cytomegalovirus promoter [Foecking et al., *Gene* 45: 101 (1980) ].

Alternatively, a prokaryotic promoter, such as the bacteriophage T3 RNA polymerase promoter, can be used to control fusion gene expression if the prokaryotic promoter is regulated by a eukaryotic promoter. Zhou et al., *Mol. Cell. Biol.* 10: 4529 (1990); Kaufman et al., *Nucl. Acids Res.* 19: 4485 (1991).

An expression vector can be introduced into host cells using a variety of techniques including calcium phosphate transfection, liposome-mediated transfection, electroporation, and the like. Preferably, transfected cells are selected and propagated wherein the expression vector is stably integrated in the host cell genome to produce stable transformants. Techniques for introducing vectors into eukaryotic cells and techniques for selecting stable transformants using a dominant selectable marker are described, for example, by Ausubel and by Murray (ed.), GENE TRANSFER AND EXPRESSION PROTOCOLS (Humana Press 1991).

2. Use of DNA Molecules Encoding RFC to Detect the Expression of the RFC Gene DNA molecules encoding the RFC gene can be used to detect the level of RFC gene expression in tissue samples. Such a detection method can be used, for example, to compare the amount of RFC RNA in a sample obtained from normal tissue and in a sample isolated from methotrexate-resistant tumor tissue. The presence of relatively low levels of RFC RNA in the tumor sample would indicate that methotrexate resistance is due, at least in part, to underexpression of the RFC gene. This result also would indicate that treatment of a mammal having such a tumor with methotrexate should be augmented by RFC gene therapy, as described below.

In testing a tissue sample for RFC RNA using a nucleic acid hybridization assay, RNA can be isolated from tissue by sectioning on a cryostat and lysing the sections with a detergent such as SDS and a chelating agent such as EDTA, optionally with overnight digestion with proteinase K. Such tissue is obtained by biopsy. A preferred quantity of tissue is in the range of 1–10 milligrams. Protein is removed by phenol and chloroform extractions, and nucleic acids are precipitated with ethanol. RNA is isolated by chromatography on an oligo dT column and then eluted from the column. Further fractionation also can be carried out according to methods well known to those of ordinary skill in the art.

A number of techniques for molecular hybridization are used for the detection of DNA or RNA sequences in tissues. When large amounts of tissue are available, analysis of hybridization kinetics provides the opportunity to accurately quantitate the amount of DNA or RNA present, as well as to distinguish sequences that are closely related but not identical to the probe.

Reactions are run under conditions of hybridization (Tm-25° C.) in which the rate of reassociation of the probe is optimal. Wetmur et al., *J. Mol. Biol.* 31: 349 (1968). The kinetics of the reaction are second-order when the sequences in the tissue are identical to those of the probe; however, the reaction exhibits complex kinetics when probe sequences have partial homology to those in the tissue. Sharp et al., *J. Mol. Biol.* 86: 709 (1974).

The concentration of probe to cellular RNA is determined by the sensitivity desired. To detect one transcript per cell would require about 100 pg of probe per μg of total cellular DNA or RNA. The nucleic acids are mixed, denatured, brought to the appropriate salt concentration and temperature, and allowed to hybridize for various periods of time. The rate of reassociation can be determined by quantitating the amount of probe hybridized either by hydroxyapatite chromatography (Britten et al., *Science* 161: 529 (1968)) or by S1 nuclease digestion (Sutton, *Biochem. Biophys. Acta* 240: 522 (1971).

A more flexible method of hybridization is the northern blot technique. Northern analysis can be performed as described herein.

The particular hybridization technique is not essential to the invention, and any technique commonly used in the art being within the scope of the present invention. Typical probe technology is described in U.S. Pat. No. 4,358,535 to Falkow et al., incorporated by reference herein. For example, hybridization can be carried out in a solution containing 6×SSC (10×SSC: 1.5M sodium chloride, 0.15M sodium citrate, pH 7.0), 5×Denhardt's (1×Denhardt's: 0.2% bovine serum albumin, 0.2% polyvinylpyrrolidone, 0.02% Ficoll 400), 10 mM EDTA, 0.5% SDS and about $10^7$ cpm of nick-translated DNA for 16 hours at 65° C.

Labeled DNA or RNA probes provide a general diagnostic method for detection of an RFC RNA in tumor tissue. The method is reasonably rapid, has a simple protocol, has reagents which can be standardized and provided as commercial kits, and allows for rapid screening of large numbers of samples.

The hybridization assays of the present invention are particularly well suited for preparation and commercialization in kit form, the kit comprising a carrier means compartmentalized to receive one or more container means (vial, test tube, etc.) in close confinement, with each container means comprising one of the separate elements to be used in hybridization assay.

For example, there may be a container means containing RFC DNA molecules suitable for labeling by "nick translation," or containing labeled RFC DNA or labeled RFC RNA molecules. Further container means may contain standard solutions for nick translation of DNA comprising DNA polymerase I/DNase I and unlabeled deoxyribonucleotides.

3. Use of DNA Molecules Encoding RFC to Increase Methotrexate Uptake of Mammalian Cells The present invention also contemplates a method for the restoration of RFC activity, and thus MTX sensitivity, in a MTX-resistant, transport-deficient cancer cell. The method comprises the construction of a vector containing the gene encoding RFC, and the introduction of the recombinant vector into a MTX-resistant, transport-deficient cancer cell. Such gene therapy will enhance the efficacy of traditional methotrexate chemotherapy, which is administered according to established protocols.

The construction of a recombinant vector containing the gene encoding RFC according to the invention can be achieved by any of the methods well-known in the art for the insertion of exogenous DNA into a vector. See, e.g., Maniatis et al., *Molecular Cloning* (Cold Spring Harbor Press 2d ed. 1989), which is incorporated herein by reference. In addition, the prior art teaches various methods of introducing exogenous genes into cells in vivo. See Rosenberg et al., *Science* 242: 1575–1578 (1988) and Wolff et al., *PNAS* 86: 9011–9014 (1989), which are incorporated herein by reference. The routes of delivery include systemic administration and administration in situ. Well-known techniques include systemic administration with cationic liposomes, and administration in situ with viral vectors. Any one of the gene delivery methodologies described in the prior art is suitable for the introduction of a recombinant vector containing the gene encoding RFC according to the invention into a MTX-resistant, transport-deficient cancer cell. A listing of present-day vectors suitable for the purpose of this invention is set forth in Hodgson, *Bio/Technology* 13: 222 (1995), which is incorporated by reference.

For example, liposome-mediated gene transfer is a suitable method for the introduction of a recombinant vector containing the gene encoding RFC according to the invention into a MTX-resistant, transport-deficient cancer cell. The use of a cationic liposome, such as DC-Chol/DOPE liposome, has been widely documented as an appropriate vehicle to deliver DNA to a wide range of tissues through intravenous injection of DNA/cationic liposome complexes. See Caplen et al., *Nature Med.* 1: 39–46 (1995) and Zhu et al., *Science* 261: 209–211 (1993), which are herein incorporated by reference. Liposomes transfer genes to the target cells by fusing with the plasma membrane. The entry process is relatively efficient, but once inside the cell, the liposome-DNA complex has no inherent mechanism to deliver the DNA to the nucleus. As such, the most of the lipid and DNA gets shunted to cytoplasmic waste systems and destroyed. The obvious advantage of liposomes as a gene therapy vector is that liposomes contain no proteins, which thus minimizes the potential of host immune responses.

As another example, viral vector-mediated gene transfer is also a suitable method for the introduction of a recombinant vector containing the gene encoding RFC according to the invention into a MTX-resistant, transport-deficient cancer cell. Appropriate viral vectors include adenovirus vectors and adeno-associated virus vectors, retrovirus vectors and herpesvirus vectors.

Adenovirus vectors can be used to introduce the gene encoding RFC according to the invention into a MTX-resistant, transport-deficient cancer cell. Adenoviruses are linear, double stranded DNA viruses complexed with core proteins and surrounded by capsid proteins. The common serotypes 2 and 5, which are not associated with any human malignancies, are typically the base vectors. By deleting parts of the virus genome and inserting the desired gene under the control of a constitutive viral promoter, the virus becomes a replication deficient vector capable of transferring the exogenous DNA to differentiated, non-proliferating cells. To enter cells, the adenovirus fibre interacts with specific receptors on the cell surface, and the adenovirus surface proteins interact with the cell surface integrins. The virus penton-cell integrin interaction provides the signal that brings the exogenous gene-containing virus into a cytoplasmic endosome. The adenovirus breaks out of the endosome and moves to the nucleus, the viral capsid falls apart, and the exogenous DNA enters the cell nucleus where it functions, in an epichromosomal fashion, to express the exogenous gene. Detailed discussions of the use of adenoviral vectors for gene therapy can be found in Berkner, *Biotechniques* 6: 616–629 (1988) and Trapnell, *Advanced Drug Delivery Rev.* 12: 185–199 (1993), which are herein incorporated by reference. Adenovirus-derived vectors, particularly non-replicative adenovirus vectors, are characterized by their ability to accommodate exogenous DNA of 7.5 kB, relative stability, wide host range, low pathogenicity in man, and high titers ($10^4$ to $10^5$ plaque forming units per cell). See Stratford-Perricaudet et al., *PNAS* 89: 2581 (1992).

Adeno-associated virus (AAV) vectors can be used also to introduce the gene encoding RFC according to the invention into a MTX-resistant, transport-deficient cancer cell. AAV is a linear single-stranded DNA parvovirus that is endogenous to many mammalian species. AAV has a broad host range despite the limitation that AAV is a defective parvovirus which is dependent totally on either adenovirus or herpesvirus for its reproduction in vivo. The use of AAV as a vector for the introduction into target cells of exogenous DNA is well-known in the art. See, e.g., Lebkowski et al., *Mole. & Cell. Biol.* 8: 3988 (1988), which is incorporated herein by reference. In these vectors, the capsid gene of AAV is replaced by a desired DNA fragment, and transcomplementation of the deleted capsid function is used to create a recombinant virus stock. Upon infection the recombinant virus uncoats in the nucleus and integrates into the host genome.

Another suitable virus-based gene delivery mechanism is retroviral vector-mediated gene transfer. In general, retroviral vectors are well-known in the art. See Breakefield et al., *Mole. Neuro. Biol.* 1: 339 (1987) and Shih et al., in *Vaccines* 85: 177 (Cold Spring Harbor Press 1985). A variety of retroviral vectors and retrovital vector-producing cell lines can be used to introduce DNA encoding RFC into MTX-deficient, transport-deficient cancer cells. Appropriate retrovital vectors include Moloney Murine Leukemia Virus, spleen necrosis virus, and vectors derived from retroviruses such as Rous Sarcoma Virus, Harvey Sarcoma Virus, arian leukosis virus, human immunodeficiency virus, myeloproliferative sarcoma virus, and mammary tumor virus. These vectors include replication-competent and replication-defective retroviral vectors. In addition, amphotropic and xenotropic retroviral vectors can be used. In carrying out the invention, retroviral vectors can be introduced to a tumor directly or in the form of free retroviral vector producing-cell lines. Suitable producer cells include fibroblasts, neurons, glial cells, keratinocytes, hepatocytes, connective tissue cells, ependymal cells, chromaffin cells. See Wolff et al., *PNAS* 84: 3344 (1989).

Retroviral vectors generally are constructed such that the majority of its structural genes are deleted or replaced by exogenous DNA of interest, and such that the likelihood is reduced that viral proteins will be expressed. See Bender et al., *J. Virol.* 61: 1639 (1987) and Armentano et al., *J. Virol.* 61: 1647 (1987), which are herein incorporated by reference. To facilitate the restoration of RFC activity, a retroviral vector employed in the present invention must integrate into the genome of the host cell genome, an event which occurs only in mitotically active cells. The necessity for host cell replication effectively limits retroviral gene expression to tumor cells, which are highly replicative, and to a few normal tissues. The normal tissue cells theoretically most likely to be transduced by a retrovital vector, therefore, are the endothelial cells that line the blood vessels that supply blood to the tumor. In addition, it is also possible that a retrovital vector would integrate into white blood cells both in the tumor or in the blood circulating through the tumor.

The spread of retroviral vector to normal tissues, however, is limited. The local administration to a tumor of a retroviral vector or retroviral vector producing cells will restrict vector propagation to the local region of the tumor, minimizing transduction, integration, expression and subsequent cytotoxic effect on surrounding cells that are mitotically active.

Both replicatively deficient and replicatively competent retroviral vectors can be used in the invention, subject to their respective advantages and disadvantages. For instance, for tumors that have spread regionally, such as lung cancers, the direct injection of cell lines that produce replication-deficient vectors may not deliver the vector to a large enough area to completely eradicate the tumor, since the vector will be released only form the original producer cells and their progeny, and diffusion is limited. Similar constraints apply to the application of replication deficient vectors to tumors that grow slowly, such as human breast cancers which typically have doubling times of 30 days versus the 24 hours common among human gliomas. The much shortened survival-time of the producer cells, probably no more than 7–14 days in the absence of immunosuppression, limits to only a portion of their replicative cycle the exposure of the tumor cells to the retroviral vector.

The use of replication-defective retroviruses for treating tumors requires producer cells and is limited because each replication-defective retrovirus particle can enter only a single cell and cannot productively infect others thereafter. Because these replication-defective retroviruses cannot spread to other tumor cells, they would be unable to completely penetrate a deep, multilayered tumor in vivo. See Markeft et al., Neurosurg. 77: 590 (1992). The injection of a replication-competent retroviral vector particles or a cell line that produces a replication-competent retroviral vector virus may prove to be a more effective therapeutic because a replication competent retroviral vector will establish a productive infection that will transduce cells as long as it persists. Moreover, replicatively competent retroviral vectors may follow the tumor as it metastasizes, carried along and propagated by transduced tumor cells. The risks for complications are greater, with replicatively competent vectors, however. Such vectors may pose a greater risk then replicatively deficient vectors of transducing normal tissues, for instance. The risks of undesired vector propagation for each type of cancer and affected body area can be weighed against the advantages in the situation of replicatively competent verses replicatively deficient retroviral vector to determine an optimum treatment.

Both amphotropic and xenotropic retroviral vectors may be used in the invention. Amphotropic virus have a very broad host range that includes most or all mammalian cells, as is well known to the art. Xenotropic viruses can infect all mammalian cell cells except mouse cells. Thus, amphotropic and xenotropic retroviruses from many species, including cows, sheep, pigs, dogs, cats, rats, and mice, inter alia can be used to provide retroviral vectors in accordance with the invention, provided the vectors can transfer genes into proliferating human cells in vivo.

Clinical trials employing retroviral vector therapy treatment of cancer have been approved in the United States. See Culver, Clin. Chem. 40: 510 (1994). Retroviral vector-containing cells have been implanted into brain tumors growing in human patients. See Oldfield et al., Hum. Gene Ther. 4: 39 (1993). These retroviral vectors carried the HSV-1 thymidine kinase (HSV-tk) gene into the surrounding brain tumor cells, which conferred sensitivity of the tumor cells to the antiviral drug ganciclovir. Some of the limitations of current retroviral based cancer therapy, as described by Oldfield are: (1) the low titer of virus produced, (2) virus spread is limited to the region surrounding the producer cell implant, (3) possible immune response to the producer cell line, (4) possible insertional mutagenesis and transformation of retroviral infected cells, (5) only a single treatment regimen of pro-drug, ganciclovir, is possible because the "suicide" product kills retrovirally infected cells and producer cells and (6) the bystander effect is limited to cells in direct contact with retrovirally transformed cells. See Bi et al., Human Gene Therapy 4: 725 (1993).

Yet another suitable virus-based gene delivery mechanism is herpesvirus vector-mediated gene transfer. While much less is known about the use of herpesvirus vectors, replication-competent HSV-1 viral vectors have been described in the context of antitumor therapy. See Martuza et al., Science 252: 854 (1991), which is incorporated herein by reference.

It is expected that one skilled in the art having the benefit of the foregoing disclosure and the references cited therein would recognize the relative strengths and weaknesses of each gene delivery system in determining an appropriate method for the introduction of a recombinant vector containing the gene encoding RFC according to the invention into a MTX-resistant, transport-deficient cancer cell.

4. Production of RFC Antibodies and RFC Antibody Fragments

Antibodies to human reduced folate carrier protein can be obtained using the product of an RFC expression vector as an antigen. As an illustration, Example 5 shows the use of a rabbit anti-RFC polyclonal preparation in which a hydrophilic portion of RFC1 was used to stimulate antibody production. The preparation of polyclonal antibodies is well-known to those of skill in the art. See, for example, Green et al., "Production of Polyclonal Antisera," in IMMUNOCHEMICAL PROTOCOLS (Manson, ed.), pages 1–5 (Humana Press 1992).

Alternatively, an RFC antibody of the present invention may be derived from a rodent monoclonal antibody (MAb). Rodent monoclonal antibodies to specific antigens may be obtained by methods known to those skilled in the art. See, for example, Kohler and Milstein, Nature 256: 495 (1975), and Coligan et al. (eds.), CURRENT PROTOCOLS IN IMMUNOLOGY, VOL. 1, pages 2.5.1–2.6.7 (John Wiley & Sons 1991) [hereinafter "Coligan"]. Briefly, monoclonal antibodies can be obtained by injecting mice with a composition comprising an antigen, verifying the presence of antibody production by removing a serum sample, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

MAbs can be isolated and purified from hybridoma cultures by a variety of well-established techniques. Such isolation techniques include affinity chromatography with Protein-A Sepharose, size-exclusion chromatography, and ion-exchange chromatography. See, for example, Coligan at pages 2.7.1–2.7.12 and pages 2.9.1–2.9.3. Also, see Baines et al., "Purification of Immunoglobulin G (IgG)," in METHODS IN MOLECULAR BIOLOGY, VOL. 10, pages 79–104 (The Humana Press, Inc. 1992).

An RFC antibody of the present invention may also be derived from a subhuman primate antibody. General techniques for raising therapeutically useful antibodies in baboons may be found, for example, in Goldenberg et al., international patent publication No. WO 91/11465 (1991), and in Losman et al., Int. J. Cancer 46: 310 (1990), which is incorporated by reference.

Alternatively, a therapeutically useful RFC antibody may be derived from a "humanized" monoclonal antibody.

Humanized monoclonal antibodies are produced by transferring mouse complementary determining regions from heavy and light variable chains of the mouse immunoglobulin into a human variable domain, and then, substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by the publication of Orlandi et al., *Proc. Nat'l Acad. Sci. USA* 86: 3833 (1989), which is incorporated by reference in its entirety. Techniques for producing humanized MAbs are described, for example, by Jones et al., *Nature* 321: 522 (1986), Riechmann et al., *Nature* 332: 323 (1988), Verhoeyen et al., *Science* 239: 1534 (1988), Carter et al., *Proc. Nat'l Acad. Sci. USA* 89: 4285 (1992), Sandhu, *Crit. Rev. Biotech.* 12: 437 (1992), and Singer et al., *J. Immun.* 150: 2844 (1993), each of which is hereby incorporated by reference.

As an alternative, an RFC antibody of the present invention may be derived from human antibody fragments isolated from a combinatorial immunoglobulin library. See, for example, Barbas et al., *METHODS: A Companion to Methods in Enzymology* 2:119 (1991), and Winter et al., *Ann. Rev. Immunol.* 12:433 (1994), which are incorporated by reference. Cloning and expression vectors that are useful for producing a human immunoglobulin phage library can be obtained, for example, from STRATAGENE Cloning Systems (La Jolla, Calif.).

In addition, an RFC antibody of the present invention may be derived from a human monoclonal antibody. Such antibodies are obtained from transgenic mice that have been "engineered" to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described by Green et al., *Nature Genet.* 7: 13 (1994), Lonberg et al., *Nature* 368: 856 (1994), and Taylor et al., *Int. Immun.* 6:579 (1994), which are incorporated by reference.

RFC antibody fragments can be prepared by proteolytic hydrolysis of the antibody or by expression in *E. coli* of the DNA coding for the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab fragments and an Fc fragment directly. These methods are described, for example, by Goldenberg, U.S. Pat. Nos. 4,036,945 and 4,331,647 and references contained therein, which patents are incorporated herein in their entireties by reference. Also, see Nisonoff et al., *Arch Biochem. Biophys.* 89: 230 (1960); Porter, *Biochem. J.* 73: 119 (1959), Edelman et al., in *METHODS IN ENZYMOLOGY VOL.* 1, page 422 (Academic Press 1967), and Coligan at pages 2.8.1–2.8.10 and 2.10.–2.10.4.

Other methods of cleaving antibodies, such as separation of heavy chains to form monovalent light-heavy chain fragments, further cleavage of fragments, or other enzymatic, chemical or genetic techniques may also be used, so long as the fragments bind to the antigen that is recognized by the intact antibody.

For example, Fv fragments comprise an association of $V_H$ and $V_L$ chains. This association can be noncovalent, as described in Inbar et al., *Proc. Nat'l Acad. Sci. USA* 69: 2659 (1972). Alternatively, the variable chains can be linked by an intermolecular disulfide bond or cross-linked by chemicals such as glutaraldehyde. See, for example, Sandhu, supra.

Preferably, the Fv fragments comprise $V_H$ and $V_L$ chains which are connected by a peptide linker. These single-chain antigen binding proteins (sFv) are prepared by constructing a structural gene comprising DNA sequences encoding the $V_H$ and $V_L$ domains which are connected by an oligonucleotide. The structural gene is inserted into an expression vector which is subsequently introduced into a host cell, such as *E. coli*. The recombinant host cells synthesize a single polypeptide chain with a linker peptide bridging the two V domains. Methods for producing sFvs are described, for example, by Whitlow et al., *Methods: A Companion to Methods in Enzymology* 2: 97 (1991). Also see Bird et al., *Science* 242: 423–426 (1988), Ladner et al., U.S. Pat. No. 4,946,778, Pack et al., *Bio/Technology* 11:1271–1277 (1993), and Sandhu, supra.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick et al., *Methods: A Companion to Methods in Enzymology* 2: 106 (1991).

5. Use of RFC Antibodies to Detect RFC Protein

The present invention contemplates the use of RFC to screen biological samples in vitro for the expression of reduced folate carrier by tumor cells. For example, the RFC antibodies of the present invention can be used to detect the presence reduced folate carrier in tissue sections prepared from a biopsy specimen. Such immunochemical detection can be used to determine both the abundance and the distribution of reduced folate carrier in the examined tissue. Moreover, immunological detection is useful to screen potential patients for therapy with the RFC gene. General immunochemistry techniques are well-known to those of ordinary skill. See, for example, Ponder, "Cell Marking Techniques and Their Application," in MAMMALIAN DEVELOPMENT: A PRACTICAL APPROACH, Monk (ed.), pages 115–38 (IRL Press 1987), Volm et al., *Eur. J. Cancer Clin. Oncol.* 25: 743 (1989), Coligan at pages 5.8.1–5.8.8, and Ausubel et al. (eds.), CURRENT PROTOCOLS IN MOLECULAR BIOLOGY, pages 14.6.1 to 14.6.13 (Wiley Interscience 1990). Also, see generally, Manson (ed.), METHODS IN MOLECULAR BIOLOGY, VOL. 10: IMMUNOCHEMICAL PROTOCOLS (The Humana Press, Inc. 1992).

Immunochemical detection can be performed by contacting a biological sample with an RFC antibody or with an RFC antibody fragment, and then contacting the biological sample with a detectably labeled molecule which binds to an RFC antibody or to an RFC antibody fragment. For example, the detectably labeled molecule can comprise an antibody moiety that binds an RFC antibody. Alternatively, an RFC antibody or fragment can be conjugated with avidin/streptavidin (or biotin) and the detectably labeled molecule can comprise biotin (or avidin/streptavidin). Numerous variations of this basic technique are well-known to those of skill in the art.

Alternatively, an RFC antibody can be conjugated with a diagnostic agent. For example, an RFC antibody can be detectably labeled with any appropriate marker moiety, for example, a radioisotope, a fluorescent label, a chemiluminescent label, an enzyme label, a bioluminescent label or colloidal gold. Methods of making and detecting such detectably-labeled "RFC immunoconjugates" are well-known to those of ordinary skill in the art, and are described in more detail below.

The marker moiety can be a radioisotope that is detected by autoradiography. Isotopes that are particularly useful for the purpose of the present invention are $^3H$, $^{125}I$, $^{131}I$, $^{35}S$ and $^{14}C$.

RFC immunoconjugates also can be labeled with a fluorescent compound. The presence of a fluorescently-labeled antibody component is determined by exposing the RFC immunoconjugate to light of the proper wavelength and detecting the resultant fluorescence. Fluorescent labeling compounds include fluorescein isothiocyanate, rhodamine, phycoerytherin, phycocyanin, allophycocyanin, o-phthaldehyde and fluorescamine.

Alternatively, RFC immunoconjugates can be detectably labeled by coupling an antibody component to a chemiluminescent compound. The presence of the chemiluminescent-tagged RFC immunoconjugate is determined by detecting the presence of luminescence that arises during the course of a chemical reaction. Examples of chemiluminescent labeling compounds include luminol, isoluminol, an aromatic acridinium ester, an imidazole, an acridinium salt and an oxalate ester.

Similarly, a bioluminescent compound can be used to label RFC immunoconjugates of the present invention. Bioluminescence is a type of chemiluminescence found in biological systems in which a catalytic protein increases the efficiency of the chemiluminescent reaction. The presence of a bioluminescent protein is determined by detecting the presence of luminescence. Bioluminescent compounds that are useful for labeling include luciferin, luciferase and aequorin.

Alternatively, RFC immunoconjugates can be detectably labeled by linking an antibody component to an enzyme. When the RFC immunoconjugate-enzyme conjugate is incubated in the presence of the appropriate substrate, the enzyme moiety reacts with the substrate to produce a chemical moiety which can be detected, for example, by spectrophotometric, fluorometric or visual means. Examples of enzymes that can be used to detectably label polyspecific immunoconjugates include β-galactosidase, glucose oxidase, peroxidase and alkaline phosphatase.

Those of skill in the art will know of other suitable labels which can be employed in accordance with the present invention. The binding of marker moieties to antibody components can be accomplished using standard techniques known to the art. Typical methodology in this regard is described by Kennedy et al., *Clin. Chim. Acta* 70: 1 (1976), Schurs et al., *Clin. Chim. Acta* 81: 1 (1977), Shih et al., *Int'l J. Cancer* 46: 1101 (1990), Stein et al., *Cancer Res.* 50: 1330 (1990), supra, and Stein et al., *Int. J. Cancer* 55: 938 (1993). Also, see generally, Coligan.

In addition, the convenience and versatility of immunochemical detection can be enhanced by using antibody components that have been conjugated with avidin, streptavidin, and biotin. See, for example, Wilchek et al. (eds.), *Avidin-Biotin Technology*, METHODS IN ENZYMOLOGY, VOL. 184 (Academic Press 1990), and Bayer et al., "Immunochemical Applications of Avidin-Biotin Technology," in METHODS IN MOLECULAR BIOLOGY, VOL. 10, Manson (ed.), pages 149–162 (The Human Press, Inc. 1992).

Thus, the above-described immunochemical detection methods can be used to assist in the diagnosis or staging of a pathological condition. Suitable methods include in vitro assays, such as the enzyme-linked immunosorbant assay and Western analysis. Other suitable in vitro assays will be readily apparent to those of skill in the art. See, generally, METHODS IN MOLECULAR BIOLOGY, VOL. 10, Manson (ed.), (The Humana Press, Inc. 1992).

RFC antibodies also can be used to detect the presence of RFC protein in tissue sections prepared from a histological specimen. Such in situ detection can be accomplished by applying a detectably-labeled RFC antibody or RFC antibody fragment to the tissue sections. In situ detection can be used to determine the presence of RFC protein and to determine the distribution of the protein in the examined tissue. General techniques of in situ detection are well-known to those of ordinary skill. See, for example, Ponder, "Cell Marking Techniques and Their Application," in MAMMALIAN DEVELOPMENT: A PRACTICAL APPROACH 113–38 Monk (ed.) (IRL Press 1987), and Coligan.

The present invention, thus generally described, will be understood more readily by reference to the following examples, which are provided by way of illustration and are not intended to be limiting of the present invention.

EXAMPLE 1

Isolation of DNA Molecules Encoding the Human Reduced Folate Carrier Gene

MTX$^R$ZR-75-1 is a methotrexate-resistant human breast cancer cell line that has undetectable levels of both folate receptor and RFC activity. Dixon et al., *Cancer Commun.* 3: 357 (1991). A murine RFC cDNA clone was isolated by expressing an L1210 cDNA library in MTX$^R$ZR-75-1 cells and by selecting the transfected cells with trimetrexate, a methotrexate analog which enters cells by diffusion, in the presence of low concentrations of folinic acid. Dixon et al., *J. Biol. Chem.* 269: 17 (1994).

Figure 1:
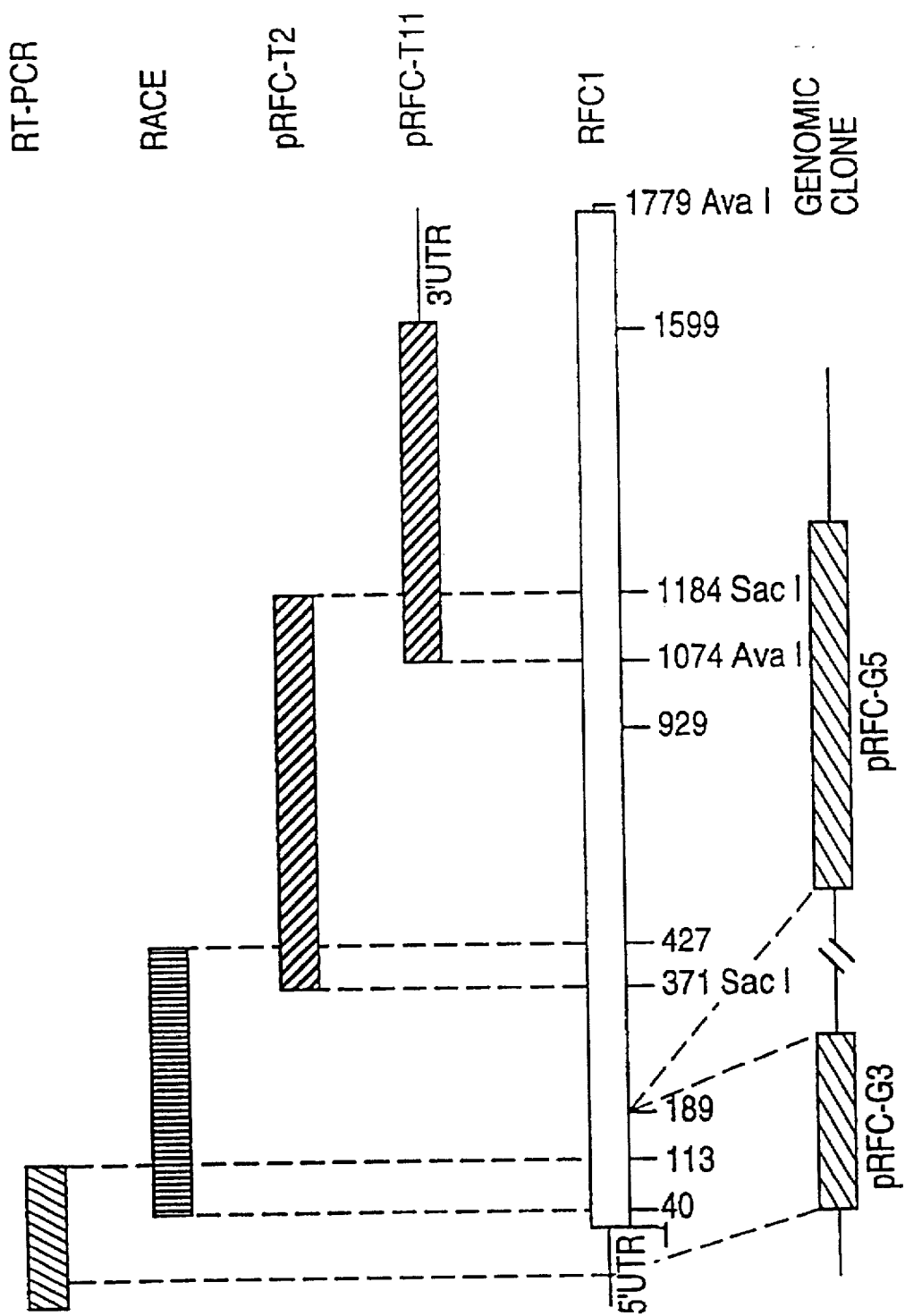
FIG. 1 is a diagram of cDNA, RACE, RT-PCR and genomic fragments of RFC1. pRFC-T2 and pRFC-T11 are partial cDNA clones, while pRFC-G3 and pRFC-G5 are contiguous genomic XbaI fragments. Position +1 indicates the translation start site.

A human testis cDNA library (Clontech) was screened using the murine RFC cDNA clone as a probe following standard techniques. After screening 600,000 plaques, two overlapping cDNA clones were isolated. cDNA inserts from both clones were ligated into pGEM-3Z (Promega). Nucleotide sequence analysis demonstrated that the 5' clone, pRFC-T2 overlapped the 3' clone, pRFC-T11 by 130 base pairs. See FIG. 1.

Several attempts to obtain a full-length cDNA clone by screening other libraries were unsuccessful. Consequently, a human leukocyte genomic EMBL3 library (Clontech) was screened using pRPC-T2, and a single 20 kilobase (kb) genomic fragment was isolated by standard plaque hybridization techniques. The 20 kb fragment was cleaved with XbaI into three fragments of 4, 6, and 10 kb, and the fragments were inserted into pGEM-3Z. Southern hybridization with the pRFC-T2 cDNA clone revealed that the 6 kb fragment, designated as pRFC-G5, contains at least part of the upstream cDNA pRFC-T2 sequence. Similar studies using the murine cDNA probe indicated that the 10 kb fragment, designated as pRFC-G3, contains the 5'-end of the RFC coding region.

EXAMPLE 2

Nucleotide Sequence Analyses of Human RFC Clones

Rapid amplification of cDNA ends (RACE) was used to determine the nucleotide sequence of the 5' region of RFC1, as well as to confirm the sequence of the RFC1 exon in pRFC-G5. In these studies, nucleotide sequences were determined using Sequenase (United States Biochemical). The reaction mixtures were fractionated on a 6% denaturing acrylamide gel using standard procedures. Custom oligonucleotide primers for sequencing were purchased from Midland Certified Reagent Company (Midland, Tex.).

RACE-ready cDNA prepared from human liver RNA (Clontech) was amplified with nested, RFC1-specific downstream primers. The nucleotide sequence isolated by this technique did not contain the start of translation, but did contain sequences upstream of the 5' intron-exon border in pRFC-G5 which also were present in pRFC-G3. Primers corresponding to the RACE sequence allowed nucleic acid sequencing of the 5' exon present in pRFC-G3, which confirmed the nucleotide sequence obtained by RACE.

The 5' end of the RFC coding region also was amplified by reverse transcriptase-polymerase chain reaction (RT-PCR) with RNA from ZR75-1 cells, using primers derived from the genomic sequence of pRFC-G3. The nucleotide sequence of the RT-PCR fragment was determined using a thermal cycling sequencing kit (Stratagene) with primers that had been end-labeled with [γ$^{33}$P]ATP and T4 DNA polynucleotide kinase (Promega). The sequencing reactions were performed in a Perkin Elmer 9600 thermal cycler and size-fractionated on a 6% polyacrylamide gel. The nucleotide sequence obtained from the RT-PCR fragment confirmed the sequence obtained from pRFC-G3.

As described above, cDNA clones, pRFC-T2 and pRFC-T11, overlap by 130 base pairs. The nucleotide sequences of the overlapping region was found to be identical. The nucleotide sequence of this region also was found to be identical with the nucleotide sequence in the overlapping genomic clone, pRFC-G5.

Nucleotide sequence analysis of the genomic and cDNA clones revealed that RFC1 was organized into at least three exons. The two identified intron/exon borders are at nucleotides 189 and 929. The nucleotide sequence of the RFC1 coding region and the 3' untranslated region (UTR), in addition to the predicted amino acid sequence, is shown in FIG. 2. The 3' region of the downstream cDNA clone, pRFC-T11, contains the TGA stop condon, but does not contain a polyadenylation signal in the 3' UTR. The nucleotide sequence is approximately 70% homologous to previously reported murine and hamster RFC genes. Dixon et al. (1994), supra; Williams et al., *J. Biol. Chem.* 269:5810 (1994).

The predicted human RFC1 protein product, hRFC1, has a molecular weight of 59 kDa and an estimated pI of 9.8. The protein structure of hRFC1, like the rodent RFC genes, conforms to the structure expected of an integral membrane protein, with hydrophobic transmembrane regions flanked by hydrophilic domains. See FIG. 2. The overall amino acid homology between the human and murine proteins is 63%. The 3' end of the human gene is the least conserved region of the protein, but both the mouse and human proteins have hydrophilic carboxy termini. An N-glycosylation site at position 58, NFT, is conserved in the hamster RFC protein but not in the murine protein. A single potential phosphorylation site for protein kinase C at position 23 (RSWR) is conserved in both murine and hamster sequences (KSWR).

EXAMPLE 3

Detection of RFC Gene Expression and Gene Copy Number in Human Breast Cancer Cells To detect RFC gene expression, total RNA was isolated from ZR75-1 human breast cancer cells or from MTX$^R$ ZR-75-1 cells using a standard guanidium isothiocyanate-cesium chloride gradient centrifugation technique. The RNA was size-fractionated on a 1% agarose gel in 20 mM 3-(N-morpholino)propanesulfonic acid buffer containing 2% formaldehyde, 1 mM EDTA, and 5 mM sodium acetate. The fractionated RNA was transferred to a nylon membrane, hybridized overnight with a [$^{32}$P]-labeled pRFC-T2 insert, and washed at a final stringency of 0.1×SSC (20×SSC: 3M sodium chloride, 0.3M sodium citrate, pH 7.0) and 0.1% SDS at 65C. The results were analyzed by autoradiography. The blot was re-probed with a β-actin probe to check equivalent loading of RNA samples.

Analysis of RFC1 RNA expression in parental ZR75-1 human breast cancer cells and the transport-deficient MTX$^R$ ZR-75-1 cells revealed that the expression of the RFC gene is markedly decreased in the resistant subline compared to the parental cell line. Therefore, these results show an association between the expression of RFC1 and transport-mediated methotrexate resistance in a human cell line.

Southern analysis was performed by digesting high molecular weight DNA (15 µg) to completion with restriction endonucleases, and fractionating the digest on a 0.8% agarose gel. The DNA was depurinated in 0.25N HCl, denatured in 1.5M NaOH with 1.5M NaCl, neutralized in 1.5M NaCl in 1M Tris-HCl (pH 7.4), transferred to a nylon membrane, and hybridized overnight with a [$^{32}$P]-labeled pRFC-T2 insert. The blot was washed at a final stringency of 0.1×SSC with 0.1% SDS at 60°C. Equivalence of DNA loading was checked by ethidium bromide staining of the agarose gel, and by probing the blot with a control gene. Southern blot analysis of methotrexate-resistant cells and the parental cells revealed a decreased hybridization intensity to DNA from MTX$^R$ ZR-75-1, suggesting a decreased RFC gene copy number in these cells.

EXAMPLE 4

Localization of the RFC Gene in the Human Genome

In these studies, metaphase chromosome spreads were prepared from phytohemagglutinin-stimulated human peripheral leukocytes and from the MTX$^R$ ZR-75-1 cells using standard techniques. Dutrillaux et al., *Adv. Hum. Genet.* 5: 119 (1975). Briefly, mitotic cells shaken from colcemid-treated (0.1 mg/ml for 10 minutes to 2 hours) monolayer cultures were collected and subjected to hypotonic treatment with 0.4% KCl for 20 minutes at 37° C., and fixed with 3:1 methanol:acetic acid. GTG banding with trypsin-Giemsa was performed prior to hybridization in some experiments.

Fluorescence in situ hybridization (FISH) was performed essentially as described by Pinkel et al., *Proc. Nat'l Acad. Sci. USA* 85: 9138 (1988). RFC gene-specific primers (5'-GTGCGAAACCTCGGCTTCGGAGCT and 3'-TGTAGACGGCGCACTGTTGGTGGT) (SEQ ID NOS: 5 and 6, respectively) were used to isolate a P1 plasmid clone by PCR. These primers are contained within a single exon of the RFC gene. The identity of the P1 clone was confirmed by Southern blot hybridization with an RFC1 cDNA probe. P1 DNA containing RFC1 was directly labeled with Spectrum Orange-dUTP (Vysis; Naperville, Ill.) by nick-translation.

In each hybridization, 100 ng of probe DNA was used in a final volume of 10 µl containing 50% formamide, 10% dextran sulfate, 2×SSC and 10 µg COT1 DNA (Bethesda Research Laboratories, Inc.). The hybridization mixture was denatured at 70° C. for five minutes and immediately applied to denatured metaphase spreads. Hybridization was carried out overnight in a moist chamber at 37° C. Slides were washed three times in 50% formamide/2×SSC (pH 7.0) at 45° C. for 5 minutes each. Three additional washes were performed in 2×SSC at 45° C. (5 minutes each) followed by a final wash in 2×SSC/0.1% Nonidet P40 for 5 minutes. The slides were dehydrated in an ethanol series and stained with 0.5 mg/ml 4,6-diamidino-2-phenylindole (DAPI) DNA counterstain. A Zeiss Axiophot microscope equipped with a cooled charge-coupled device camera was used for image acquisition.

Eighteen normal metaphase spreads of normal human lymphocytes were examined and distinct fluorescent signals were observed on chromosome 21. All of the hybridization signals examined were present on the chromatids of both homologs. Fluorescence in situ hybridization on normal, elongated BrdU-treated chromosomes was performed to further refine the localization of the RFC gene to the tip of the long arm of chromosome 21 (21q22.2-q22.3).

The RFC1 gene copy number in both parental and MTX$^R$ ZR-75-1 cells was determined using the FISH technique. The results revealed four copies of RFC1 in the parental cell line; two copies are arranged in tandem on a marker chromosome which contains 21q material. One sub-population of parental cells has, in addition, two other normal copies of chromosome 21, while another sub-population has one normal chromosome 21 and one rearranged chromosome 21. In contrast, MTX$^R$ ZR-75-1 cells have only two normal copies of chromosome 21 and have lost the marker chromosome.

EXAMPLE 5

Detection of RFC Protein Using RFC Antibody

Western blot analyses were performed using a rabbit polyclonal antibody that had been raised against a hydrophilic region of RFC1. In these studies, proteins from parental cells and MTX$^R$ ZR-75-1 cells were harvested in a buffer of 62.5 mM Tris-HCl (pH 6.8), 2 mM EDTA, 15% sucrose, 10% glycerol, 3% SDS and 5% 2-mercaptoethanol. Fifty micrograms of protein from each cellular lysate were resolved by polyacrylamide gel electrophoresis on a 10% acrylamide gel, according to the method of Laemmli, Nature 227: 680 (1970). The gels were electroblotted onto a nitrocellulose membrane in transfer buffer containing 48 mM Tris-HCl, 39 mM glycine, 0.037% SDS in 20% methanol for two hours. The nitrocellulose membrane was incubated with a blocking solution (10 mM Tris-HCl, 5% nonfat milk, 0.01% Tween-20) for two hours, and then incubated with the rabbit RFC antibody (at a dilution of 1:10,000) for two hours at room temperature. The membrane was washed with Tris-buffered saline containing 0.1% Tween-20, incubated with an anti-rabbit antibody-horseradish peroxidase conjugate (BioRad), washed again with Tris-buffered saline containing 0.1% Tween-20, and developed using a phosphorescence detection kit (Amersham).

These studies revealed a decreased expression of an approximately 56 kDa protein in the methotrexate-resistant cell line, compared with the parental cell line. A faint 63 kDa band also can be observed in the cellular protein of the parental line. It is possible that the 56 kDa protein is a processed or degraded form of human RFC.

EXAMPLE 6

Transfection of Human Cells with RFC DNA

To study the function of reduced folate carrier, cells were transfected with DNA encoding the RFC gene. In these studies, DNA molecules containing the RFC1 coding region were obtained with RT-PCR using primers flanking the RFC coding region and RNA isolated from MCF-7 human breast cancer cells. The PCR product was subcloned into the SmaI-digested and alkaline phosphatase-treated pREP3 vector, which is a eukaryotic expression vector. Dixon et al. (1994), supra. The 5'- and 3'-ends of the ligated insert were confirmed by DNA sequencing. MTX$^R$ZR-75-1 cells were transfected with a plasmid containing an RFC insert ("MTX$^R$ZR75-pREP/RFC1"), or with pREP3 lacking the RFC insert ("MTX$^R$ZR75-pREP") by a standard calcium chloride precipitation technique. Cells were selected in 200 µg/ml hygromycin. Surviving clones were pooled for further analysis.

To examine effect of RFC gene transfection on methotrexate uptake, transfected MTX$^R$ZR-75-1 cells were plated at a density of $1 \times 10^5$ in 6-well Linbro dishes in folate-free IMEM with 5% fetal bovine serum, 100 µM hypothanxine, 16 µM thymidine and 200 µg/ml hygromycin. After 48–72 hours of growth, the cells were exposed to 2 µM [$^3$H] methotrexate for 15 minutes in folate-free IMEM medium supplemented with 20 mM HEPES (pH 7.2) at 37° C.

The transport medium was aspirated and the plates were immersed in three successive washes of ice-cold Dulbecco's phosphate buffered saline. The cells were solubilized by overnight incubation in 0.2N NaOH, neutralized with 0.2N HCl, and radioactivity was determined by liquid scintillation counting. Protein concentrations were determined by Bradford assay. Non-specific binding was determined by exposure of cells to transport medium for less than 5 seconds, and was subtracted from the 15 minute uptake to indicate specific uptake. Competitors were added in 100-fold molar excess.

Figure 4:
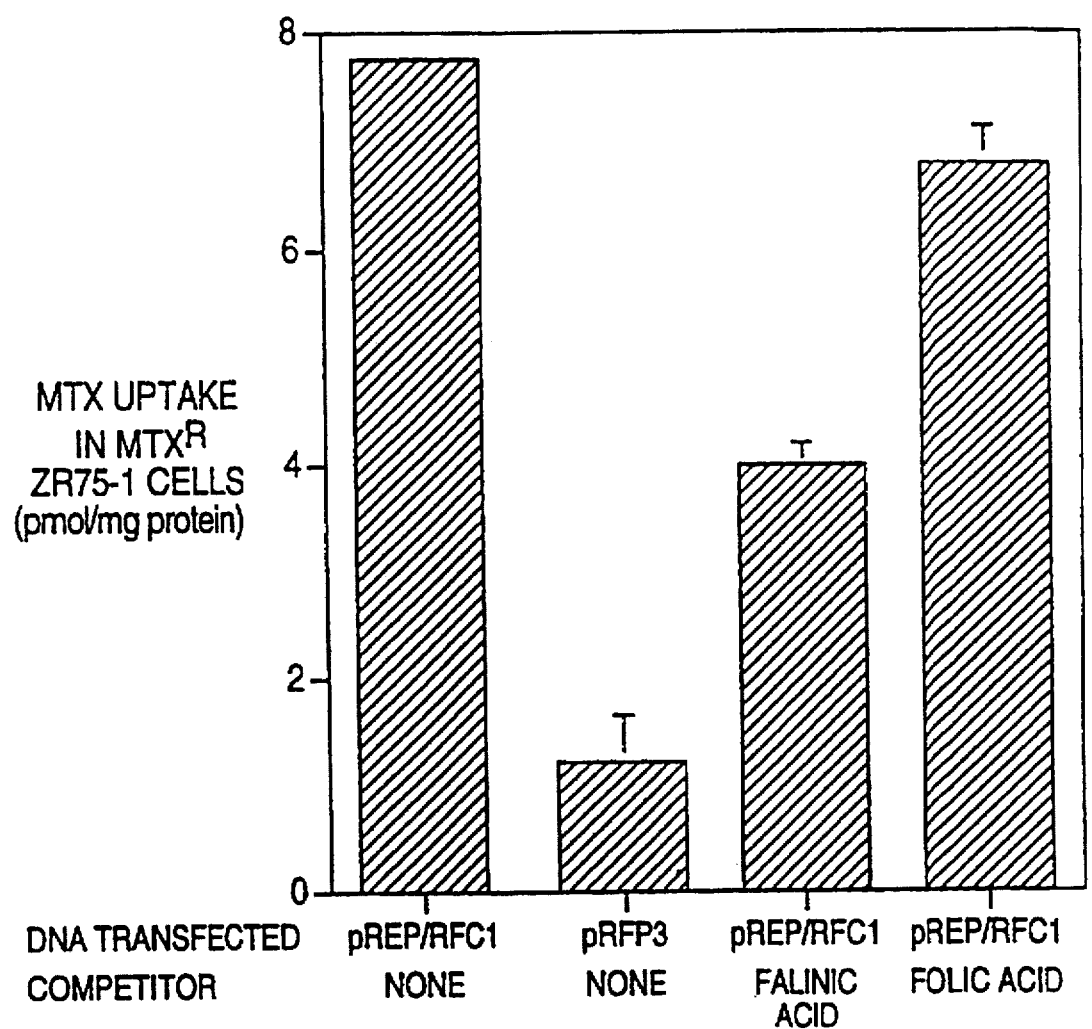
FIG. 4 shows methotrexate uptake by $MTX^R$ZR-75-1 cells with an RFC1 expression vector (pREP/RFC1) or with an empty vector (pREP3). In these studies, cells were incubated with radiolabeled methotrexate in the absence or in the presence of a molar excess of the indicated competitors.

As shown in FIG. 4, methotrexate uptake was about six-fold greater in cells that had been transfected with the RFC1 gene. Moreover, methotrexate uptake was inhibited to a greater extent by folinic acid, compared with folic acid. This is a property that is characteristic of the function of the reduced folate carrier. The results of these studies indicate that methotrexate uptake by human cells can be increased by transfection of cells with DNA encoding the RFC gene.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following claims.

All publications and patent applications mentioned in this specification are indicative of the level of skill of those in the art to which the invention pertains. All publications and patent applications are herein incorporated by reference to the same extent as if each individual publication or patent application were specifically and individually indicated to be incorporated by reference in its entirety.

What is claimed is:

1. An antibody that binds to human reduced folate carrier (RFC) protein, wherein said RFC protein comprises a polypeptide having the amino acid sequence of SEQ ID NO: 2.

2. The antibody of claim 1, wherein said antibody is a polyclonal antibody.

3. The antibody of claim 1, wherein said antibody is a monoclonal antibody.

4. A method of using the antibody of claim 1 to detect the presence of RFC protein in a biological sample, said method comprising the steps of:

(a) contacting said biological sample with said antibody, (b) detecting said antibody bound to said biological sample, and (c) determining the presence of RFC protein based on the detection of bound antibody.

5. The method of claim 4, wherein the presence of RFC protein is determined by in situ detection of bound antibody.

6. An immunoconjugate comprising an antibody or an antibody fragment that binds to human reduced folate carrier (RFC) protein, wherein said RFC protein comprises a polypeptide having the amino acid sequence of SEQ ID NO: 2, and a detectable label.

7. The immunoconjugate of claim 6, wherein said detectable label is selected from the group consisting of a radioactive label, photoactive agent or dye, fluorescent label, enzyme label, bioluminescent label, chemiluminescent label and colloidal gold.

\* \* \* \* \*

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
( A ) LENGTH: 1776 base pairs
( B ) TYPE: nucleic acid
( C ) STRANDEDNESS: single
( D ) TOPOLOGY: linear ( i x ) FEATURE:
( A ) NAME/KEY: CDS
( B ) LOCATION: 1..1773

( x i ) SEQUENCE DESCRIPTION: SEQ ID NO:1:

```
ATG GTG CCC TCC AGC CCA GCG GTG GAG AAG CAG GTG CCC GTG GAA CCT        48
Met Val Pro Ser Ser Pro Ala Val Glu Lys Gln Val Pro Val Glu Pro
 1               5                  10                  15

GGG CCT GAC CCC GAG CTC CGG TCC TGG CGG CGC CTC GTG TGC TAC CTT        96
Gly Pro Asp Pro Glu Leu Arg Ser Trp Arg Arg Leu Val Cys Tyr Leu
            20                  25                  30

TGC TTC TAC GGC TTC ATG GCG CAG ATA CGG CCA GGG GAG AGC TTC ATC       144
Cys Phe Tyr Gly Phe Met Ala Gln Ile Arg Pro Gly Glu Ser Phe Ile
        35                  40                  45

ACC CCC TAC CTC CTG GGG CCC GAC AAG AAC TTC ACG CGG GAC GAG GTC       192
Thr Pro Tyr Leu Leu Gly Pro Asp Lys Asn Phe Thr Arg Asp Glu Val
    50                  55                  60

ACG AAC GAG ATC ACG CCG GTG CTG TCG TAC TCC TAC CTG GCC GTG CTG       240
Thr Asn Glu Ile Thr Pro Val Leu Ser Tyr Ser Tyr Leu Ala Val Leu
65                  70                  75                  80

GTG CCC GTG TTC CTG CTC ACC GAC TAC CTG CGC TAC ACG CCG GTG CTG       288
Val Pro Val Phe Leu Leu Thr Asp Tyr Leu Arg Tyr Thr Pro Val Leu
                85                  90                  95

CTG CTG CAG GGG CTC AGC TTC GTG TCG GTG TGG CTG CTG CTG CTG CTG       336
Leu Leu Gln Gly Leu Ser Phe Val Ser Val Trp Leu Leu Leu Leu Leu
            100                 105                 110

GGC CAC TCG GTG GCG CAC ATG CAG CTC ATG GAG CTC TTC TAC AGC GTC       384
Gly His Ser Val Ala His Met Gln Leu Met Glu Leu Phe Tyr Ser Val
        115                 120                 125

ACC ATG GCC GCG CGC ATC GCC TAT TCC TCC TAC ATC TTC TCT CTC GTG       432
Thr Met Ala Ala Arg Ile Ala Tyr Ser Ser Tyr Ile Phe Ser Leu Val
    130                 135                 140

CGG CCC GCG CGC TAC CAG CGT GTG GCC GGC TAC TCG CGC GCT GCG GTG       480
Arg Pro Ala Arg Tyr Gln Arg Val Ala Gly Tyr Ser Arg Ala Ala Val
145                 150                 155                 160

CTG CTG GGC GTG TTC ACC AGC TCC GTG CTG GGC CAG CTG CTG GTC ACT       528
Leu Leu Gly Val Phe Thr Ser Ser Val Leu Gly Gln Leu Leu Val Thr
                165                 170                 175

GTG GGC CGA GTC TCC TTC TCC ACG CTC AAC TAC ATC TCG CTG GCC TTC       576
Val Gly Arg Val Ser Phe Ser Thr Leu Asn Tyr Ile Ser Leu Ala Phe
            180                 185                 190

CTC ACC TTC AGC GTG GTC CTC GCC CTC TTC CTG AAG CGC CCC AAG CGC       624
Leu Thr Phe Ser Val Val Leu Ala Leu Phe Leu Lys Arg Pro Lys Arg
        195                 200                 205

AGC CTC TTC TTC AAC CGC GAC GAC CGG GGG CGG TGC GAA ACC TCG GCT       672
Ser Leu Phe Phe Asn Arg Asp Asp Arg Gly Arg Cys Glu Thr Ser Ala
    210                 215                 220
```

| | | | | | | | | | | | | | | | | |
|---|---|---|---|---|---|---|---|---|---|---|---|---|---|---|---|---|
| TCG | GAG | CTG | GAG | CGC | ATG | AAT | CCT | GGC | CCA | GGC | GGG | AAG | CTG | GGA | CAC | 720 |
| Ser 225 | Glu | Leu | Glu | Arg | Met 230 | Asn | Pro | Gly | Pro 235 | Gly | Gly | Lys | Leu | Gly | His 240 | |
| GCC | CTG | CGG | GTG | GCC | TGT | GGG | GAC | TCA | GTG | CTG | GCG | CGG | ATG | CTG | CGG | 768 |
| Ala | Leu | Arg | Val 245 | Ala | Cys | Gly | Asp | Ser 250 | Val | Leu | Ala | Arg | Met 255 | Leu | Arg | |
| GAG | CTG | GGG | GAC | AGC | CTG | CGG | CGG | CCG | CAG | CTG | CGC | CTG | TGG | TCC | CTC | 816 |
| Glu | Leu | Gly | Asp 260 | Ser | Leu | Arg | Arg | Pro 265 | Gln | Leu | Arg | Leu | Trp 270 | Ser | Leu | |
| TGG | TGG | GTC | TTC | AAC | TCG | GCC | GGC | TAC | TAC | CTG | GTG | GTC | TAC | TAC | GTG | 864 |
| Trp | Trp | Val 275 | Phe | Asn | Ser | Ala | Gly 280 | Tyr | Tyr | Leu | Val | Val 285 | Tyr | Tyr | Val | |
| CAC | ATC | CTG | TGG | AAC | GAG | GTG | GAC | CCC | ACC | ACC | AAC | AGT | GCG | CGG | GTC | 912 |
| His | Ile | Leu 290 | Trp | Asn | Glu | Val | Asp 295 | Pro | Thr | Thr | Asn | Ser 300 | Ala | Arg | Val | |
| TAC | AAC | GGC | GCG | GCA | GAT | GCT | GCC | TCC | ACG | CTG | CTG | GGC | GCC | ATC | ACG | 960 |
| Tyr | Asn | Gly | Ala 310 | Ala | Asp | Ala | Ala | Ser 315 | Thr | Leu | Leu | Gly | Ala 320 | Ile | Thr | |
| Tyr 305 | | | | | | | | | | | | | | | | |
| TCC | TTC | GCC | GCG | GGC | TTC | GTG | AAG | ATC | CGC | TGG | GCG | CGC | TGG | TCC | AAG | 1008 |
| Ser | Phe | Ala | Ala | Gly 325 | Phe | Val | Lys | Ile | Arg 330 | Trp | Ala | Arg | Trp | Ser 335 | Lys | |
| CTG | CTC | ATC | GCG | GGC | GTC | ACG | GCC | ACG | CAG | GCG | GGG | CTG | GTC | TTC | CTT | 1056 |
| Leu | Leu | Ile | Ala 340 | Gly | Val | Thr | Ala | Thr 345 | Gln | Ala | Gly | Leu | Val 350 | Phe | Leu | |
| CTG | GCG | CAC | ACG | CGC | CAC | CCG | AGC | AGC | ATC | TGG | CTG | TGC | TAT | GCG | GCC | 1104 |
| Leu | Ala | His 355 | Thr | Arg | His | Pro | Ser 360 | Ser | Ile | Trp | Leu | Cys 365 | Tyr | Ala | Ala | |
| TTC | GTG | CTG | TTC | CGC | GGC | TCC | TAC | CAG | TTC | CTC | GTG | CCC | ATC | GCC | ACC | 1152 |
| Phe | Val 370 | Leu | Phe | Arg | Gly | Ser 375 | Tyr | Gln | Phe | Leu | Val 380 | Pro | Ile | Ala | Thr | |
| TTT | CAG | ATT | GCA | TCT | TCT | CTG | TCT | AAA | GAG | CTC | TGT | GCC | CTG | GTC | TTC | 1200 |
| Phe 385 | Gln | Ile | Ala | Ser | Ser 390 | Leu | Ser | Lys | Glu | Leu 395 | Cys | Ala | Leu | Val | Phe 400 | |
| GGG | GTC | AAC | ACG | TTC | TTT | GCC | ACC | ATC | GTC | AAG | ACC | ATC | ATC | ACT | TTC | 1248 |
| Gly | Val | Asn | Thr | Phe 405 | Phe | Ala | Thr | Ile | Val 410 | Lys | Thr | Ile | Ile | Thr 415 | Phe | |
| ATT | GTC | TCG | GAC | GTG | CGG | GGC | CTG | GGC | CTC | CCG | GTC | CGC | AAG | CAG | TTC | 1296 |
| Ile | Val | Ser | Asp 420 | Val | Arg | Gly | Leu | Gly 425 | Leu | Pro | Val | Arg | Lys 430 | Gln | Phe | |
| CAG | TTA | TAC | TCC | GTG | TAC | TTC | CTG | ATC | CTG | TCC | ATC | ATC | TAC | TTC | TTG | 1344 |
| Gln | Leu | Tyr 435 | Ser | Val | Tyr | Phe | Leu 440 | Ile | Leu | Ser | Ile | Ile 445 | Tyr | Phe | Leu | |
| GGG | GCC | ATG | CTG | GAT | GGC | CTG | CGC | GAC | TGC | CAG | CGG | GGC | CAC | CAC | CCG | 1392 |
| Gly | Ala | Met 450 | Leu | Asp | Gly | Leu | Arg 455 | Asp | Cys | Gln | Arg | Gly 460 | His | His | Pro | |
| CGG | CAG | CCC | CCG | GCC | CAG | GGC | CTG | AGG | AGT | GCC | GCG | GAG | GAG | AAG | GCA | 1440 |
| Arg 465 | Gln | Pro | Pro | Ala | Gln 470 | Gly | Leu | Arg | Ser | Ala 475 | Ala | Glu | Glu | Lys | Ala 480 | |
| GCA | CAG | CGA | CTG | AGC | GTG | CAG | GAC | AAG | GGC | CTC | GGA | GGC | CTG | CAG | CCA | 1488 |
| Ala | Gln | Arg | Leu | Ser 485 | Val | Gln | Asp | Lys 490 | Gly | Leu | Gly | Gly | Leu 495 | Gln | Pro | |
| GCC | CAG | AGC | CCG | CCG | CTT | TCC | CCA | GAA | GAC | AGC | CTG | GGG | GCT | GTG | GGG | 1536 |
| Ala | Gln | Ser | Pro 500 | Pro | Leu | Ser | Pro | Glu 505 | Asp | Ser | Leu | Gly | Ala 510 | Val | Gly | |
| CCA | GCC | TCC | CTG | GAG | CAG | AGA | CAG | AGC | GAC | CCA | TAC | CTG | GCC | CAG | GCC | 1584 |
| Pro | Ala | Ser | Leu 515 | Glu | Gln | Arg | Gln | Ser 520 | Asp | Pro | Tyr | Leu 525 | Ala | Gln | Ala | |
| CCG | GCC | CCG | CAG | GCA | GCT | GAA | TTC | CTG | AGC | CCA | GTG | ACA | ACC | CCT | TCC | 1632 |
| Pro | Ala | Pro | Gln | Ala | Ala 535 | Glu | Phe | Leu | Ser | Pro 540 | Val | Thr | Thr | Pro | Ser | |
| 530 | | | | | | | | | | | | | | | | |

| CCC | TGC | ACT | CTG | TCG | TCC | GCC | CAA | GCC | TCA | GGC | CCT | GAG | GCT | GCA | GAT | 1680 |
| Pro | Cys | Thr | Leu | Ser | Ser | Ala | Gln | Ala | Ser | Gly | Pro | Glu | Ala | Ala | Asp | |
| 545 | | | | 550 | | | | | 555 | | | | | 560 | | |

| GAG | ACT | TGT | CCC | CAG | CTG | GCT | GTC | CAT | CCT | CCT | GGT | GTC | AGC | AAG | CTG | 1728 |
| Glu | Thr | Cys | Pro | Gln | Leu | Ala | Val | His | Pro | Pro | Gly | Val | Ser | Lys | Leu | |
| | | | | 565 | | | | | 570 | | | | | 575 | | |

| GGT | TTG | CAG | TGT | CTT | CCA | AGC | GAC | GGT | GTT | CAG | AAT | GTG | AAC | CAG | | 1773 |
| Gly | Leu | Gln | Cys | Leu | Pro | Ser | Asp | Gly | Val | Gln | Asn | Val | Asn | Gln | | |
| | | | 580 | | | | | 585 | | | | | 590 | | | |

TGA                                                                                                          1776

( 2 ) INFORMATION FOR SEQ ID NO:2:

( i ) SEQUENCE CHARACTERISTICS:
        ( A ) LENGTH: 591 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Val | Pro | Ser | Ser | Pro | Ala | Val | Glu | Lys | Gln | Val | Pro | Val | Glu | Pro |
| 1 | | | | 5 | | | | | 10 | | | | | 15 | |

| Gly | Pro | Asp | Pro | Glu | Leu | Arg | Ser | Trp | Arg | Arg | Leu | Val | Cys | Tyr | Leu |
| | | | 20 | | | | | 25 | | | | | 30 | | |

| Cys | Phe | Tyr | Gly | Phe | Met | Ala | Gln | Ile | Arg | Pro | Gly | Glu | Ser | Phe | Ile |
| | | 35 | | | | | 40 | | | | | 45 | | | |

| Thr | Pro | Tyr | Leu | Leu | Gly | Pro | Asp | Lys | Asn | Phe | Thr | Arg | Asp | Glu | Val |
| | 50 | | | | | 55 | | | | | 60 | | | | |

| Thr | Asn | Glu | Ile | Thr | Pro | Val | Leu | Ser | Tyr | Ser | Tyr | Leu | Ala | Val | Leu |
| 65 | | | | | 70 | | | | 75 | | | | | | 80 |

| Val | Pro | Val | Phe | Leu | Leu | Thr | Asp | Tyr | Leu | Arg | Tyr | Thr | Pro | Val | Leu |
| | | | | 85 | | | | | 90 | | | | | 95 | |

| Leu | Leu | Gln | Gly | Leu | Ser | Phe | Val | Ser | Val | Trp | Leu | Leu | Leu | Leu | Leu |
| | | | 100 | | | | | 105 | | | | | 110 | | |

| Gly | His | Ser | Val | Ala | His | Met | Gln | Leu | Met | Glu | Leu | Phe | Tyr | Ser | Val |
| | | 115 | | | | | 120 | | | | | 125 | | | |

| Thr | Met | Ala | Ala | Arg | Ile | Ala | Tyr | Ser | Ser | Tyr | Ile | Phe | Ser | Leu | Val |
| | 130 | | | | | 135 | | | | | 140 | | | | |

| Arg | Pro | Ala | Arg | Tyr | Gln | Arg | Val | Ala | Gly | Tyr | Ser | Arg | Ala | Ala | Val |
| 145 | | | | | 150 | | | | 155 | | | | | | 160 |

| Leu | Leu | Gly | Val | Phe | Thr | Ser | Ser | Val | Leu | Gly | Gln | Leu | Leu | Val | Thr |
| | | | | 165 | | | | | 170 | | | | | 175 | |

| Val | Gly | Arg | Val | Ser | Phe | Ser | Thr | Leu | Asn | Tyr | Ile | Ser | Leu | Ala | Phe |
| | | | 180 | | | | | 185 | | | | | 190 | | |

| Leu | Thr | Phe | Ser | Val | Val | Leu | Ala | Leu | Phe | Leu | Lys | Arg | Pro | Lys | Arg |
| | | 195 | | | | | 200 | | | | | 205 | | | |

| Ser | Leu | Phe | Phe | Asn | Arg | Asp | Asp | Arg | Gly | Arg | Cys | Glu | Thr | Ser | Ala |
| | 210 | | | | | 215 | | | | | 220 | | | | |

| Ser | Glu | Leu | Glu | Arg | Met | Asn | Pro | Gly | Pro | Gly | Gly | Lys | Leu | Gly | His |
| 225 | | | | | 230 | | | | 235 | | | | | | 240 |

| Ala | Leu | Arg | Val | Ala | Cys | Gly | Asp | Ser | Val | Leu | Ala | Arg | Met | Leu | Arg |
| | | | | 245 | | | | | 250 | | | | | 255 | |

| Glu | Leu | Gly | Asp | Ser | Leu | Arg | Arg | Pro | Gln | Leu | Arg | Leu | Trp | Ser | Leu |
| | | | 260 | | | | | 265 | | | | | 270 | | |

| Trp | Trp | Val | Phe | Asn | Ser | Ala | Gly | Tyr | Tyr | Leu | Val | Val | Tyr | Tyr | Val |
| | | 275 | | | | | 280 | | | | | 285 | | | |

| His | Ile | Leu | Trp | Asn | Glu | Val | Asp | Pro | Thr | Thr | Asn | Ser | Ala | Arg | Val |
|---|---|---|---|---|---|---|---|---|---|---|---|---|---|---|---|
| | 290 | | | | 295 | | | | | 300 | | | | | |
| Tyr | Asn | Gly | Ala | Ala | Asp | Ala | Ala | Ser | Thr | Leu | Leu | Gly | Ala | Ile | Thr |
| 305 | | | | | 310 | | | | | 315 | | | | | 320 |
| Ser | Phe | Ala | Ala | Gly | Phe | Val | Lys | Ile | Arg | Trp | Ala | Arg | Trp | Ser | Lys |
| | | | | 325 | | | | | 330 | | | | | 335 | |
| Leu | Leu | Ile | Ala | Gly | Val | Thr | Ala | Thr | Gln | Ala | Gly | Leu | Val | Phe | Leu |
| | | | | 340 | | | | | 345 | | | | 350 | | |
| Leu | Ala | His | Thr | Arg | His | Pro | Ser | Ser | Ile | Trp | Leu | Cys | Tyr | Ala | Ala |
| | | | 355 | | | | 360 | | | | | 365 | | | |
| Phe | Val | Leu | Phe | Arg | Gly | Ser | Tyr | Gln | Phe | Leu | Val | Pro | Ile | Ala | Thr |
| | 370 | | | | | 375 | | | | | 380 | | | | |
| Phe | Gln | Ile | Ala | Ser | Ser | Leu | Ser | Lys | Glu | Leu | Cys | Ala | Leu | Val | Phe |
| 385 | | | | | 390 | | | | | 395 | | | | | 400 |
| Gly | Val | Asn | Thr | Phe | Phe | Ala | Thr | Ile | Val | Lys | Thr | Ile | Ile | Thr | Phe |
| | | | | 405 | | | | | 410 | | | | | 415 | |
| Ile | Val | Ser | Asp | Val | Arg | Gly | Leu | Gly | Leu | Pro | Val | Arg | Lys | Gln | Phe |
| | | | 420 | | | | | 425 | | | | | 430 | | |
| Gln | Leu | Tyr | Ser | Val | Tyr | Phe | Leu | Ile | Leu | Ser | Ile | Ile | Tyr | Phe | Leu |
| | | 435 | | | | | 440 | | | | | 445 | | | |
| Gly | Ala | Met | Leu | Asp | Gly | Leu | Arg | Asp | Cys | Gln | Arg | Gly | His | His | Pro |
| | 450 | | | | | 455 | | | | | 460 | | | | |
| Arg | Gln | Pro | Pro | Ala | Gln | Gly | Leu | Arg | Ser | Ala | Ala | Glu | Glu | Lys | Ala |
| 465 | | | | | 470 | | | | | 475 | | | | | 480 |
| Ala | Gln | Arg | Leu | Ser | Val | Gln | Asp | Lys | Gly | Leu | Gly | Leu | Gln | Pro | |
| | | | | 485 | | | | | 490 | | | | | 495 | |
| Ala | Gln | Ser | Pro | Pro | Leu | Ser | Pro | Glu | Asp | Ser | Leu | Gly | Ala | Val | Gly |
| | | | 500 | | | | | 505 | | | | | 510 | | |
| Pro | Ala | Ser | Leu | Glu | Gln | Arg | Gln | Ser | Asp | Pro | Tyr | Leu | Ala | Gln | Ala |
| | | 515 | | | | | 520 | | | | | 525 | | | |
| Pro | Ala | Pro | Gln | Ala | Ala | Glu | Phe | Leu | Ser | Pro | Val | Thr | Thr | Pro | Ser |
| | 530 | | | | | 535 | | | | | 540 | | | | |
| Pro | Cys | Thr | Leu | Ser | Ser | Ala | Gln | Ala | Ser | Gly | Pro | Glu | Ala | Ala | Asp |
| 545 | | | | | 550 | | | | | 555 | | | | | 560 |
| Glu | Thr | Cys | Pro | Gln | Leu | Ala | Val | His | Pro | Pro | Gly | Val | Ser | Lys | Leu |
| | | | | 565 | | | | | 570 | | | | | 575 | |
| Gly | Leu | Gln | Cys | Leu | Pro | Ser | Asp | Gly | Val | Gln | Asn | Val | Asn | Gln | |
| | | | 580 | | | | | 585 | | | | | 590 | | |

( 2 ) INFORMATION FOR SEQ ID NO:3:

( i ) SEQUENCE CHARACTERISTICS:
( A ) LENGTH: 502 amino acids
( B ) TYPE: amino acid
( C ) STRANDEDNESS: single
( D ) TOPOLOGY: linear ( x i ) SEQUENCE DESCRIPTION: SEQ ID NO:3:

| Met | Val | Pro | Thr | Gly | Gln | Val | Ala | Glu | Lys | Gln | Ala | Tyr | Glu | Glu | Pro |
|---|---|---|---|---|---|---|---|---|---|---|---|---|---|---|---|
| 1 | | | | 5 | | | | | 10 | | | | | 15 | |
| Arg | Gln | Asp | His | Glu | Leu | Lys | Ser | Trp | Arg | Cys | Leu | Val | Phe | Tyr | Leu |
| | | | 20 | | | | | 25 | | | | | 30 | | |
| Cys | Phe | Phe | Gly | Phe | Met | Ala | Gln | Ile | Arg | Pro | Gly | Glu | Ser | Phe | Ile |
| | | | 35 | | | | | 40 | | | | | 45 | | |
| Thr | Pro | Phe | Leu | Leu | Glu | Arg | Lys | Phe | Thr | Lys | Glu | Gln | Val | Thr | Asn |
| | | 50 | | | | | 55 | | | | | 60 | | | |

| Glu | Ile | Ile | Pro | Met | Leu | Pro | Tyr | Ser | His | Leu | Ala | Val | Leu | Val | Pro |
| 65 | | | | 70 | | | | | 75 | | | | | | 80 |
| Val | Phe | Leu | Leu | Thr | Asp | Tyr | Leu | Arg | Tyr | Lys | Pro | Val | Leu | Leu | Leu |
| | | | | 85 | | | | | 90 | | | | | 95 | |
| Gln | Cys | Leu | Ser | Phe | Val | Cys | Val | Trp | Leu | Leu | Leu | Leu | Leu | Gly | Thr |
| | | | 100 | | | | | 105 | | | | | 110 | | |
| Ser | Val | Val | His | Met | Gln | Leu | Met | Glu | Val | Phe | Tyr | Ser | Val | Thr | Met |
| | | 115 | | | | | 120 | | | | | 125 | | | |
| Ala | Ala | Arg | Ile | Ala | Tyr | Ser | Ser | Tyr | Ile | Phe | Ser | Leu | Val | His | Pro |
| | | 130 | | | | 135 | | | | | 140 | | | | |
| Ser | Arg | Tyr | Gln | Arg | Met | Ala | Ser | Tyr | Ser | Arg | Ala | Ala | Val | Leu | Leu |
| 145 | | | | | 150 | | | | | 155 | | | | | 160 |
| Gly | Val | Phe | Ile | Ser | Ser | Val | Leu | Gly | Gln | Ala | Leu | Val | Thr | Val | Gly |
| | | | | 165 | | | | | 170 | | | | | 175 | |
| His | Ile | Ser | Thr | Tyr | Thr | Leu | Asn | Cys | Val | Ser | Leu | Gly | Phe | Ile | Leu |
| | | | 180 | | | | | 185 | | | | | 190 | | |
| Phe | Ser | Leu | Val | Leu | Ser | Leu | Phe | Leu | Lys | Arg | Pro | Lys | Arg | Ser | Leu |
| | | 195 | | | | | 200 | | | | 205 | | | | |
| Phe | Phe | Asn | Arg | Ser | Thr | Leu | Ala | Arg | Gly | Ala | Leu | Pro | Cys | Glu | Leu |
| 210 | | | | | 215 | | | | | | 220 | | | | |
| Asp | Gln | Met | His | Pro | Gly | Pro | Asp | Arg | Lys | Leu | Asp | Arg | Met | Leu | Gly |
| 225 | | | | 230 | | | | | 235 | | | | | | 240 |
| Thr | Cys | Arg | Asp | Ser | Phe | Leu | Val | Arg | Met | Leu | Ser | Glu | Leu | Val | Glu |
| | | | | 245 | | | | | 250 | | | | | 255 | |
| Asn | Ala | Arg | Gln | Pro | Gln | Leu | Arg | Leu | Trp | Cys | Leu | Trp | Trp | Val | Phe |
| | | | 260 | | | | | 265 | | | | | 270 | | |
| Asn | Ser | Ser | Gly | Tyr | Tyr | Leu | Ile | Thr | Tyr | Tyr | Val | His | Val | Leu | Trp |
| | | 275 | | | | | 280 | | | | | 285 | | | |
| Arg | Ser | Thr | Asp | Ser | Ser | Leu | Ser | Tyr | Asn | Gly | Ala | Val | Asp | Ala | Ala |
| | 290 | | | | | 295 | | | | | 300 | | | | |
| Ser | Thr | Leu | Leu | Ser | Ala | Ile | Thr | Ser | Phe | Ser | Ala | Gly | Phe | Leu | Ser |
| 305 | | | | | 310 | | | | | 315 | | | | | 320 |
| Ile | Arg | Trp | Thr | Leu | Trp | Ser | Lys | Leu | Val | Ile | Ala | Gly | Val | Ile | Ala |
| | | | | 325 | | | | | 330 | | | | | | 335 |
| Ile | Gln | Ala | Ser | Leu | Val | Phe | Cys | Met | Phe | Gln | Ile | Arg | Asp | Ile | Trp |
| | | | 340 | | | | | 345 | | | | | 350 | | |
| Val | Cys | Tyr | Val | Thr | Phe | Val | Leu | Phe | Arg | Gly | Ala | Tyr | Gln | Phe | Leu |
| | | 355 | | | | | 360 | | | | | 365 | | | |
| Val | Pro | Ile | Ala | Thr | Phe | Gln | Ile | Ala | Ser | Ser | Leu | Ser | Lys | Glu | Leu |
| | 370 | | | | | 375 | | | | | 380 | | | | |
| Cys | Ala | Leu | Val | Phe | Gly | Ile | Asn | Thr | Phe | Phe | Ala | Thr | Phe | Leu | Leu |
| 385 | | | | | 390 | | | | | 395 | | | | | 400 |
| Thr | Asp | Phe | Thr | Leu | Val | Val | Ser | Asp | Lys | Arg | Gly | Leu | Gly | Leu | Gln |
| | | | | 405 | | | | | 410 | | | | | 415 | |
| Val | Arg | Asp | Gln | Phe | Arg | Ile | Tyr | Phe | Ile | Tyr | Phe | Leu | Met | Leu | Ser |
| | | | 420 | | | | | 425 | | | | | 430 | | |
| Ile | Thr | Cys | Phe | Ala | Trp | Ala | Gly | Leu | Asp | Gly | Leu | Arg | Tyr | Cys | Gln |
| | | 435 | | | | | 440 | | | | | 445 | | | |
| Arg | Gly | Arg | His | Gln | Pro | Leu | Ala | Gln | Ala | Gln | Glu | Leu | Arg | Ser | Pro |
| | 450 | | | | | 455 | | | | | 460 | | | | |
| Leu | Glu | Thr | Ser | Val | Gln | Ala | Ile | Ser | Leu | Gln | Asp | Gly | Asp | Leu | Arg |
| 465 | | | | | 470 | | | | | 475 | | | | | 480 |
| Gly | Pro | Gln | Pro | Ser | Ala | Pro | Gln | Leu | Leu | Ser | Glu | Asp | Gly | Met | Glu |

-continued

```
                        485                    490                      495

Asp  Asp  Arg  Gly  Ala  Leu
               500
```

(2) INFORMATION FOR SEQ ID NO:4:

(i) SEQUENCE CHARACTERISTICS:
        (A) LENGTH: 503 amino acids
        (B) TYPE: amino acid
        (C) STRANDEDNESS: single
        (D) TOPOLOGY: linear (xi) SEQUENCE DESCRIPTION: SEQ ID NO:4:

```
Met  Val  Pro  Thr  Gly  Gln  Val  Ala  Glu  Lys  Gln  Ala  Cys  Glu  Glu  Pro
 1                  5                        10                       15

Arg  Gln  Asp  Arg  Glu  Leu  Lys  Ser  Trp  Arg  Cys  Leu  Val  Phe  Tyr  Leu
                20                       25                       30

Cys  Phe  Phe  Gly  Phe  Met  Ala  Gln  Ile  Arg  Pro  Gly  Glu  Ser  Phe  Ile
          35                       40                       45

Thr  Pro  Tyr  Leu  Leu  Gln  Gln  Asn  Phe  Thr  Ile  Glu  Gln  Val  Thr  Asn
     50                       55                       60

Glu  Ile  Ile  Pro  Val  Leu  Pro  Tyr  Ser  His  Leu  Ala  Val  Leu  Val  Pro
65                       70                       75                       80

Ile  Phe  Leu  Leu  Thr  Asp  Tyr  Leu  Arg  Tyr  Lys  Pro  Ile  Leu  Ile  Leu
                85                       90                       95

Gln  Cys  Leu  Ser  Phe  Met  Cys  Val  Trp  Leu  Leu  Leu  Leu  Leu  Gly  Thr
               100                      105                      110

Ser  Val  Val  His  Met  Gln  Leu  Met  Glu  Val  Phe  Tyr  Ser  Val  Thr  Met
          115                      120                      125

Ala  Ala  Arg  Ile  Ala  Tyr  Ser  Ser  Tyr  Ile  Phe  Ser  Leu  Val  Arg  Pro
     130                      135                      140

Ser  Arg  Tyr  Gln  Arg  Met  Ala  Ser  Tyr  Ser  Arg  Ala  Ala  Val  Leu  Leu
145                      150                      155                      160

Gly  Val  Phe  Thr  Ser  Ser  Val  Leu  Gly  Gln  Val  Leu  Leu  Glu  Gln  Lys
               165                      170                      175

Ser  Ala  Asn  Ser  Asn  Met  Leu  Asn  Tyr  Ile  Ser  Leu  Gly  Phe  Ile  Leu
          180                      185                      190

Phe  Ser  Leu  Gly  Leu  Ser  Leu  Phe  Leu  Lys  Arg  Pro  Lys  His  Ser  Leu
     195                      200                      205

Phe  Phe  Asn  Arg  Ser  Ala  Leu  Val  His  Lys  Ala  Leu  Pro  Cys  Glu  Leu
210                      215                      220

Asp  Gln  Met  His  Pro  Gly  Pro  Gly  Gly  Lys  Leu  Glu  Arg  Val  Leu  Gly
225                      230                      235                      240

Ser  Cys  Arg  Asn  Ser  Phe  Leu  Val  Cys  Met  Leu  Ser  Glu  Leu  Val  Gly
               245                      250                      255

Asn  Leu  Arg  Gln  Pro  His  Val  Arg  Leu  Trp  Cys  Leu  Trp  Trp  Val  Phe
          260                      265                      270

Asn  Ser  Ala  Gly  Tyr  Tyr  Leu  Ile  Val  Tyr  Tyr  Val  His  Val  Leu  Trp
     275                      280                      285

Ser  Ile  Asp  Lys  Asn  Leu  Asn  Tyr  Asn  Gly  Ala  Val  Asp  Ala  Ala  Ser
290                      295                      300

Thr  Leu  Leu  Ser  Ala  Ile  Thr  Ser  Phe  Ser  Ala  Gly  Phe  Val  Lys  Ile
305                      310                      315                      320

Arg  Trp  Ala  Arg  Trp  Ser  Lys  Leu  Val  Ile  Ala  Ser  Val  Ile  Ala  Ile
               325                      330                      335

Gln  Ala  Gly  Leu  Val  Phe  Met  Val  His  Tyr  Val  Thr  Trp  Val  His  Lys
```

```
                        340                          345                          350
    Ile  Trp  Val  Leu  Tyr  Met  Thr  Tyr  Val  Leu  Phe  Arg  Gly  Ala  Tyr  Gln
              355                          360                     365

Phe  Leu  Val  Pro  Ile  Ala  Thr  Phe  Gln  Ile  Ala  Ser  Ser  Leu  Ser  Lys
         370                          375                     380

Glu  Leu  Cys  Ala  Leu  Val  Phe  Gly  Ile  Asn  Thr  Phe  Phe  Ala  Thr  Ala
    385                          390                     395                      400

Leu  Leu  Thr  Ala  Ile  Thr  Leu  Val  Val  Ser  Asp  Lys  Arg  Gly  Leu  Gly
                        405                     410                          415

Leu  Lys  Val  Glu  Asp  Gln  Phe  Cys  Ile  Tyr  Ser  Val  Tyr  Phe  Met  Val
                   420                          425                     430

Leu  Ser  Val  Ile  Cys  Phe  Val  Gly  Ala  Val  Leu  Asp  Gly  Leu  Arg  Tyr
              435                          440                     445

Cys  Arg  Arg  Gly  Arg  His  Gln  Pro  Leu  Pro  Leu  Pro  Gln  Glu  Leu  Ser
         450                          455                     460

Pro  Leu  Glu  Asn  Ser  Val  Gln  Val  Pro  Ser  Met  Gln  Asp  Arg  Asp  Leu
    465                          470                     475                      480

Gly  Gly  Leu  Gln  Pro  Ser  Ala  Pro  Gln  Leu  Leu  Pro  Glu  Asp  Gly  Val
                        485                     490                          495

Glu  Asp  Ser  Glu  Ala  Ser  Leu
                   500
```

( 2 ) INFORMATION FOR SEQ ID NO:5:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

GTGCGAAACC TCGGCTTCGG AGCT				24

( 2 ) INFORMATION FOR SEQ ID NO:6:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

TGTAGACGGC GCACTGTTGG TGGT				24